United States Patent [19]

Verlander et al.

[11] Patent Number: 4,571,345

[45] Date of Patent: Feb. 18, 1986

[54] 1,1-DIAMINOALKANE DERIVED SWEETENERS

[75] Inventors: Michael S. Verlander, Del Mar; William D. Fuller, San Diego; Murray Goodman, La Jolla, all of Calif.

[73] Assignee: Cumberland Packing Corp., Brooklyn, N.Y.

[21] Appl. No.: 503,853

[22] Filed: Jun. 13, 1983

[51] Int. Cl.$^4$ .................. A23L 1/236; A23L 1/226
[52] U.S. Cl. .................. 426/548; 426/534; 426/535; 426/536; 426/537; 426/538; 260/501.15; 562/448; 562/500; 562/502; 562/503; 562/505; 562/506; 562/507; 562/561; 568/379; 568/838; 585/20
[58] Field of Search .................. 260/501.15; 426/548, 426/534–537; 562/561, 448, 503, 505–507, 500, 502

[56] References Cited

U.S. PATENT DOCUMENTS

| | | | |
|---|---|---|---|
| 3,492,131 | 1/1970 | Schlatler | 426/548 |
| 4,338,346 | 7/1982 | Brand | 426/548 |
| 4,399,163 | 8/1983 | Brennan et al. | 426/548 |
| 4,411,925 | 10/1983 | Brennan et al. | 426/548 |
| 4,423,029 | 12/1983 | Rizzi | 426/548 X |

FOREIGN PATENT DOCUMENTS 0034876  9/1981  European Pat. Off. ............ 426/548

OTHER PUBLICATIONS

Inglett (Editor), Symposium: Sweeteners, 1974, Avi: Westport, Conn., pp. 159–163.
Hough et al (Editors), Developments in Sweeteners–I, 1979, Applied Science Publishers: London, pp. 126–133.

Primary Examiner—Joseph Golian
Attorney, Agent, or Firm—Steinberg & Raskin

[57] ABSTRACT

Compounds of the formula:

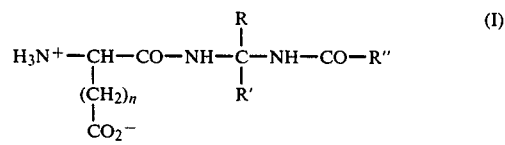

(I)

wherein n is 0 or 1, R is lower alkyl (substituted or unsubstituted), R' is H or lower alkyl, and R" is a branched alkyl, alkyl-cycloalkyl, cycloalkyl, polycycloalkyl (poly=2 or more, fused or non-fused), phenyl or alkyl-substituted phenyl, and physiologically acceptable cationic and acid addition salts thereof, which compounds are potent sweeteners. These derivatives of gem-diaminoalkanes are many times sweeter than sugar and are free from undesirable flavor qualities. Furthermore, they possess an unanticipated high degree of solubility compared with known synthetic sweeteners. In addition, the compounds possess high stability so that they can be used in all types of beverages and in conventional food processing. Sweetening compositions and sweetened edible compositions of these compounds are also provided.

19 Claims, No Drawings

1,1-DIAMINOALKANE DERIVED SWEETENERS

BACKGROUND OF THE INVENTION

The search for new sweeteners which are many times sweeter than sucrose and which are also non-caloric and non-cariogenic has been a continuing search for many years. In particular the search has been to provide new sweeteners which are not only many times sweeter than sucrose but which are free of the bitter aftertaste particularly associated with such artificial sweeteners as saccharine, and which in addition do not break down into products which are physiologically harmful and also which remain stable in aqueous systems and upon exposure to heat, for example during cooking.

U.S. Pat. No. 3,492,131 describes certain lower alkyl esters of L-aspartyl-L-phenylalanine which are up to 200 times as sweet as sucrose and which are free of bitter aftertaste. These compounds, however, possess only limited solubility in aqueous systems and are unstable due to diketopiperazine formation and hydrolysis especially in the neutral to acid pH range of most food systems (the diketopiperazine forms more slowly under acidic conditions).

European Patent Application No. 0034876, published Sept. 2, 1981, describes branched amides of L-aspartyl-D-amino acid dipeptides as sweeteners. These compounds are stated as being free of undesirable flavor qualities at conventional use levels and as having high stability both in solid form and in aqueous systems. The breakdown products thereof are not given so that the final possible uses of these sweeteners are not yet known.

SUMMARY OF THE INVENTION

It has now been found that a new series of derivatives of gem-diaminoalkanes of the formula:

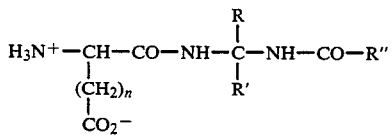

wherein n is 0 or 1, R is lower alkyl (substituted or unsubstituted), R' is H or lower alkyl, and R" is a branched alkyl, alkyl-cycloalkyl, cycloalkyl, polycycloalkyl (poly=2 or more, fused or non-fused), phenyl or alkyl-substituted phenyl, and physiologically acceptable cationic and acid addition salts thereof, possess a high degree of sweetness, without undesirable flavor notes, and in addition possess significant advantages as compared to known sweeteners.

It is accordingly a primary object of the present invention to provide a new series of sweeteners which are free of undesirable flavor notes and which possess a high degree of stability in all types of aqueous systems and even upon cooking.

It is another object of the present invention to provide a new series of sweeteners which break down only into compounds which are physiologically compatible with the body.

It is yet another object of the present invention to provide compositions for sweetening edible materials which comprise a sweetening amount of the new compounds of the invention and a nontoxic carrier.

Still further, the present invention provides sweetened edible compositions comprising an edible material and a sweetening amount of the compounds of the invention.

Still further, the invention provides a method of sweetening edible compositions by the addition thereto of a sweetening effective amount of the compounds of the invention.

The invention further provides methods for producing the new sweetening compounds thereof.

With the above and other objects in view, the present invention mainly comprises new compounds of the formula:

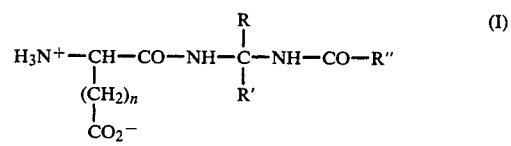

wherein n=0 or 1; R is lower alkyl, such as methyl, ethyl, n-propyl, isopropyl, isobutyl, etc., or substituted lower alkyl, such as hydroxymethyl, methyl thiomethyl, etc.; R' is H or lower alkyl, preferably methyl or ethyl; and R" is a branched alkyl group, preferably of 3–10 carbon atoms, e.g.

where $R_1$ is H or lower alkyl, preferably methyl or ethyl, $R_2$ and $R_3$ are H or lower alkyl such as methyl, ethyl, n-propyl, isopropyl, isobutyl, t-butyl, etc.; R" may also be alkyl-cycloalkyl or dicycloalkyl, i.e.

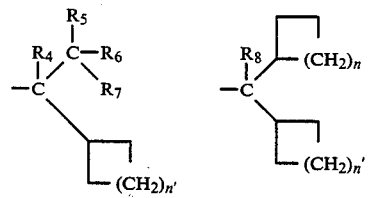

where $R_4$ and $R_8$ are H or methyl, $R_5$, $R_6$ and $R_7$ are H or lower alkyl, preferably methyl, ethyl or isopropyl, and n and n'=0, 1 or 2; R" may also be cycloalkyl, preferably of 3–7 carbon atoms, most preferably of 5–6 carbon atoms, or substituted cycloalkyl, the cycloalkyl group most preferably being of 4–6 carbon atoms and substituted by 1–4 alkyl groups, e.g.

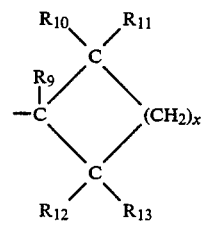

where $R_9$ is H or methyl, $R_{10}$, $R_{11}$, $R_{12}$ and $R_{13}$ are H or lower alkyl, such as methyl, ethyl, isopropyl, isobutyl, t-butyl, etc., and x=0, 1, 2 or 3; R" may also be heterocycloalkyl or alkyl-substituted heterocycloalkyl, where the heteroatom is oxygen, nitrogen or sulfur and the preferred ring size is 4-7 atoms, e.g.

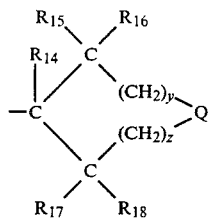

where $R_{14}$ is H or methyl, $R_{15}$, $R_{16}$, $R_{17}$ and $R_{18}$ are H or lower alkyl, such as methyl, ethyl, isopropyl, isobutyl, t-butyl, etc., y and z=0, 1 or 2, and Q is O, NH, S, SO or $SO_2$; R" may also be polycycloalkyl, such as norbornyl,

fenchyl,

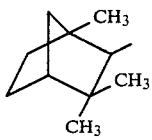

or 1- or 2-adamantyl

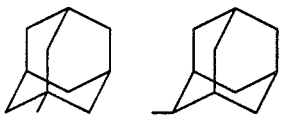

or phenyl or alkyl-substituted phenyl, the alkyl group(s) preferably being lower alkyl, e.g.

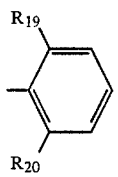

where $R_{19}$ and $R_{20}$ are H, lower alkyl such as methyl, ethyl, isopropyl, etc.

The preferred sweeteners of the present invention are those wherein R" is cycloalkyl or alkyl substituted cycloalkyl substituted by 1-5 alkyl groups, the alkyl preferably being lower alkyl.

Examples of the most valuable compounds are those wherein R" is:
tetramethylcyclopentyl,
cyclopentyl,
methylcyclohexyl,
dicyclopropylmethyl,
dimethylcyclopentyl,
trimethylcyclopentyl,
dimethylcyclohexyl,
trimethylcyclohexyl,
t-butylcyclohexyl.

As indicated above, the invention provides compositions for sweetening edible materials comprising a sweetening effective amount of a compound of the above formula along with a nontoxic carrier, for example lactose, dextrose or sucrose.

Still further, the invention provides sweetened edible compositions which comprise an edible material plus a sweetening effective amount of a compound of the invention.

Still further, the invention comprises the method of sweetening edible compositions by the addition thereto of a sweetening effective amount of a compound of the invention.

The invention further provides compositions for sweetening edible materials comprising a sweetening amount of a mixture of a compound of the invention with another artificial sweetener such as saccharine or a physiologically acceptable salt thereof, cyclamate or a physiologically compatible salt thereof, aspartame, acesulfame-K or thaumatin.

The physiologically acceptable salts of saccharine and of cyclamate are the salts thereof with physiologically acceptable cations such as sodium, potassium, calcium or ammonium.

The physiologically acceptable cationic salts of the compounds of the invention are the salts thereof formed by neutralization of the carboxylic acid group of the compounds of the invention by bases of physiologically acceptable metals, such as sodium and potassium, ammonia and amines such as N-methyl glucamine and ethanolamine.

The physiologically acceptable acid addition salts are those formed of physiologically acceptable acids such as acetic acid, benzoic acid, hydrobromic acid, hydrochloric acid, citric acid, fumaric acid, gluconic acid, lactic acid, maleic acid, malic acid, nitric, phosphoric, saccharic, succinic and tartaric acid.

DETAILED DESCRIPTION OF THE INVENTION

The following is a general scheme for the production of the gem-diaminoalkane sweeteners of the present invention:

Scheme 1

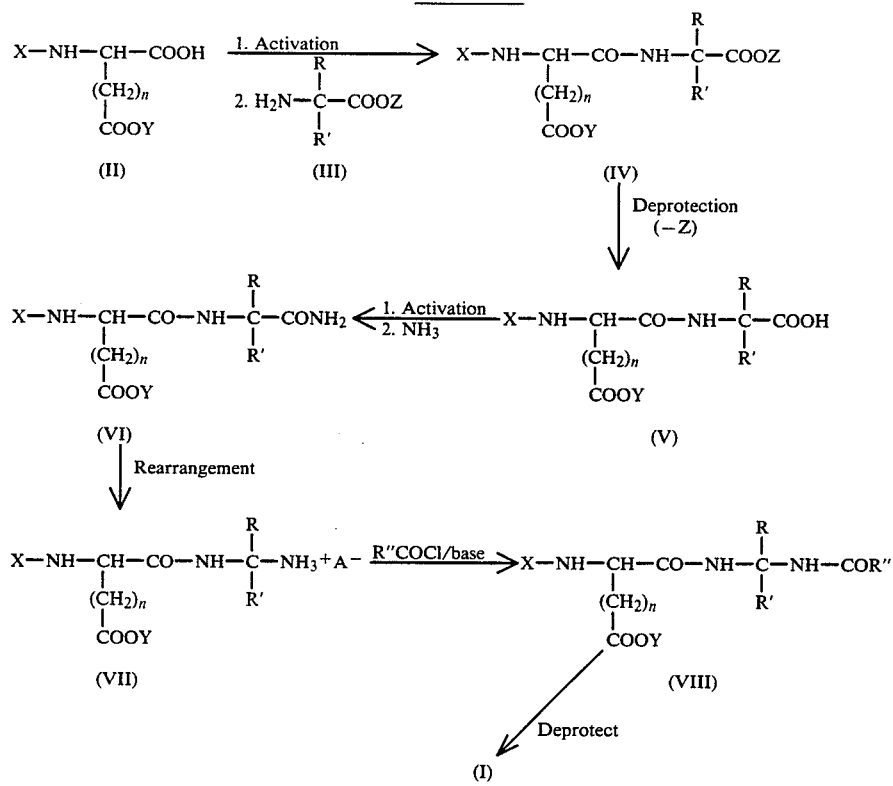

The sweeteners (I) may be synthesized by the general route outlined in Scheme 1 above. In this route, a protected aminomalonic acid derivative (II, n=0) or aspartic acid derivative (II, n=1) is employed as starting material. The amine protecting group X may be any of the groups which are commonly employed for this purpose, as described by Bodanszky et al, in "Peptide Synthesis", Wiley-Interscience, New York (1976), pp. 18–48. Particularly preferred groups are benzyloxycarbonyl, t-butyloxycarbonyl and 9-fluorenylmethyloxycarbonyl. The carboxyl-protecting group, Y, may be any of the groups which are normally used for this purpose, as described by Bodanszky et al. in "Peptide Synthesis", pp. 49–57. Preferred groups include benzyl, t-butyl or lower alkyl, such as methyl or ethyl. A particularly preferred combination of protecting groups for the protection of the amine and carboxyl functions in (II) is benzyloxycarbonyl/benzyl, since these groups may be removed selectively by hydrogenolysis under mild conditions. When use of this deprotection method is precluded, for example in compounds containing sulfur, the combination of t-butyloxycarbonyl/t-butyl, which are removable under acidic conditions, may be employed. Alternatively, the combination of 9-fluorenylmethyloxycarbonyl/benzyl or alkyl, which are cleaved simultaneously under basic conditions, may be used.

In the first step of the synthesis, the carboxyl component (II) is activated by a suitable method and coupled with an amino acid derivative (III). Any of the methods commonly used for the formation of amide bonds, as described by Bodanszky et al. in "Peptide Synthesis", pp. 85–128, may be used. However, a particularly preferred method is the mixed carboxylic-carbonic anhydride method, using isobutyl or ethyl chloroformate. The amino acid derivative (III) may be a free amino acid (i.e. Z=H) or may be a derivative in which the carboxyl group is protected by a suitable protecting group Z which may be cleaved selectively in the presence of the other protecting groups, X and Y, in the protected derivative (IV). A particularly preferred method of protection involves the use of trialkylsilyl esters (i.e. Z=trialkylsilyl), such as trimethylsilyl, since these groups may be removed under aqueous acidic conditions. In this case, removal of this protecting group may be effected during the work-up procedure, following the coupling of the carboxyl component (II) with the amino acid derivative (III), so that the partially deprotected product (IV) may be isolated directly, without the necessity for a separate deprotection step. The product (IV) may be purified, if necessary, by conventional methods, such as recrystallization or column chromatography.

The key step in the synthesis of the novel, gem-diaminoalkane-derived sweeteners of the invention involves the transformation of the carboxylic acid derivatives (V) to the monoacylated gem-diaminoalkane salts (VII). This may be accomplished by one of several standard methods, such as the Curtius rearrangement or the Schmidt rearrangement. Alternatively, the carboxylic acid derivative may first be transformed to the amide (VI) by activation and condensation with ammonia. In a preferred method, the dipeptide (V) is activated via the mixed carboxylic-carbonic anhydride at low temperature and condensed with the ammonium salt of 1-hydroxybenzotriazole. The amide (VI) may then be transformed to the gem-diaminoalkane salt (VII) via the Hofmann rearrangement using sodium hypobromite. Alternatively, a preferred reagent for effecting this transformation is iodobenzene bis(trifluoroacetate), as described by Radhakrishna et al., J. Org. Chem. 44, 1746–1747(1979).

The monoacylated gem-diaminoalkane salt (VII) is acylated by the appropriate acid chloride R"COCl under basic conditions to provide the protected sweetener derivative (VIII). This reaction may be carried out under a variety of conditions, for example in a mixture of an organic solvent such as acetonitrile and aqueous purification, for example by recrystallization, is desirable.

In an alternate route (Scheme 2), the gem-diaminoalkane derivatives (I) may be prepared by first treating the amino acid derivative (III) with the appropriate acid chloride RCOCl. As described above, the amino acid derivative (III) may be a free amino acid (i.e. Z=H) or may be

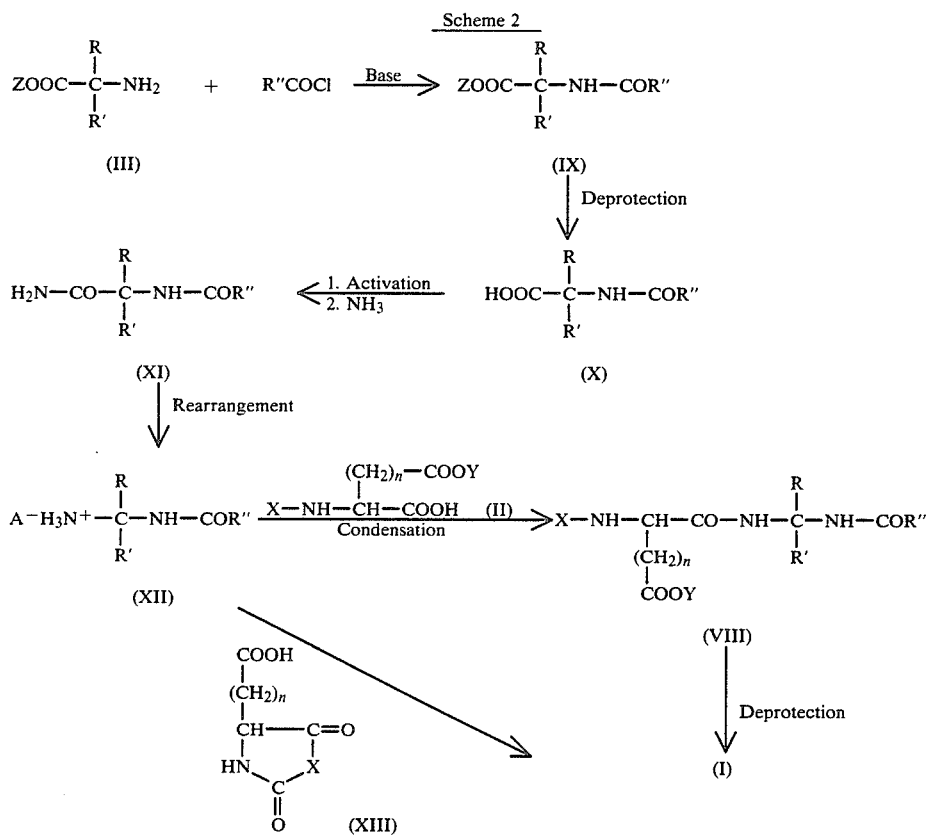

potassium bicarbonate. Alternatively, the coupling reaction may be carried out in an anhydrous organic solvent, such as tetrahydrofuran, in the presence of an equivalent of an organic base such as triethylamine. The protected sweetener derivative (VIII) may be purified if required by conventional techniques, such as recrystallization or column chromatography.

In the final step of the synthesis, the protected sweetener (VIII) is deprotected under appropriate conditions to give the final gem-diaminoalkane-derived sweetener (I). The conditions used for deprotection will depend upon the nature of the protecting groups used, i.e. X and Y. As outlined above, when the preferred combination of benzyloxycarbonyl and benzyl protecting groups is used, deprotection may be effected by hydrogenolysis at pressures of 1–10 atmospheres in the presence of a noble metal catalyst such as palladium or platinum. In the event that the molecule contains sulfur and an alternate combination of protecting groups is used, hydrolytic methods must be used for their cleavage. For example, if 9-fluorenylmethyloxycarbonyl and benzyl are used, the protecting groups may be cleaved simultaneously by basic hydrolysis, for example by treatment with excess potassium hydroxide in anhydrous methanol. While the final sweetener (I), obtained by these techniques, may be substantially pure, further carboxyl-protected. A preferred carboxyl-protecting group is the trialkylsilyl ester group, such as the trimethylsilyl group, which may be removed by aqueous acid, as described above. The next step, the key transformation of the acylated amino acid derivative (X) to the monoacylated gem-diaminoalkane salt (XII), may be accomplished by any of the methods discussed above, although the preferred route involves transformation to the primary amide derivative (XI) and rearrangement using iodobenzene bis(trifluoroacetate). Condensation of this diaminoalkane derivative (XII) with a protected aminomalonic acid or aspartic acid derivative (II) by techniques described above results in the same, fully protected sweetener derivative (VIII) as that obtained in Scheme 1. Deprotection and purification may be effected by the same techniques as those described previously.

In a preferred method, the amine salt (XII) is acylated by a cyclic derivative of aminomalonic acid or aspartic acid, such as the N-carboxyanhydride or the thiocarboxyanhydride (XIII, X=O or S). Use of these intermediates avoids the need for protection of the aminomalonic or aspartic acid residues. In yet another variation, partially protected aspartic acid derivatives, such as N-formyl aspartic anhydride, may also be used to acylate the amine salt (XII). In this case, cleavage of the formyl protecting group may be effected by treatment with aqueous acid.

The carboxylic acid chlorides R"COCl used for the synthesis of these sweeteners may be commercially available or may be synthesized by standard techniques. A preferred route for the synthesis of the carboxylic acid precursors utilizes ketones as the starting materials, as described by Martin, *Synthesis* (1979), 633–664 and is outlined in Scheme 3. By this route, the ketone (XIV) is first converted to the alkene (XVI). Several possible methods may be used for this purpose. Use of the Wittig method, involving treatment of the ketone with methylene triphenylphosphorane, results in the alkene directly. An alternate procedure, useful for ketones in which $R_{21}$ and $R_{22}$ contain tertiary carbon atoms adjacent to the ketone,

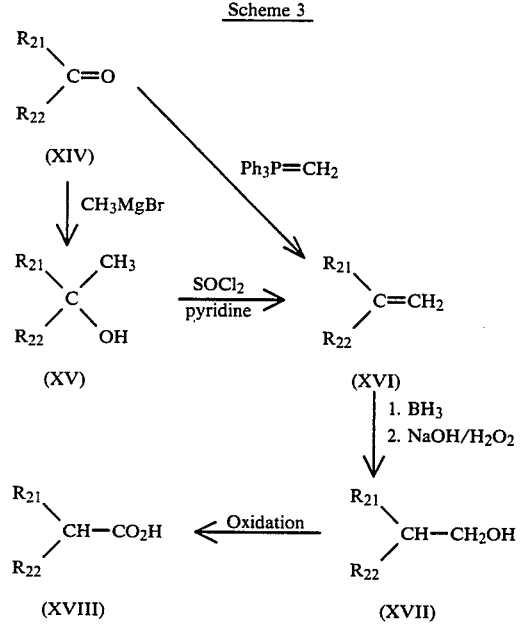

involves the two-step treatment of the ketone with methyl magnesium bromide, to give the methyl carbinol (XV), followed by dehydration with thionyl chloride in the presence of excess pyridine. The alkene (XVI) is next transformed to the alcohol (XVII) by hydroboration (treatment with borane, followed by aqueous sodium hydroxide and hydrogen peroxide). Finally, the alcohol is oxidized to the carboxylic acid (XVIII) by one of many standard techniques, such as treatment with sodium dichromate in concentrated sulfuric acid. The carboxylic acid may be transformed to the acid chloride form required for the synthesis described above by one of several standard techniques, such as treatment with thionyl chloride or phosphorus pentachloride.

The requisite ketone precursors for the carboxylic acids required for the invention are either commercially available, known in the prior art, or may be prepared by known methods. For example, the cycloalkanones and heterocycloalkanones of the general formula (XIX) and (XX), where $R_{10}$–$R_{13}$,

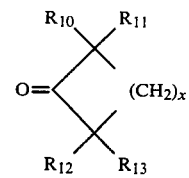

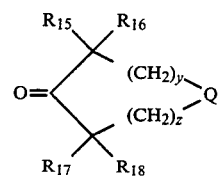

$R_{15}$–$R_{18}$, x, y, z and Q are as defined above, may be prepared by alkylation of the corresponding ketones in which $R_{10}$–$R_{13}$ and $R_{15}$–$R_{18}$ are hydrogen. Alkylation may be effected by treatment with a strong base, such as sodium hydride, sodium amide or sodium amylate, in the presence of an alkylating agent such as an alkyl halide or dialkyl sulfate.

The methods described above are provided for the purpose of illustrating the invention but in no way are meant to limit the scope of the invention. Alternate methods, obvious to those skilled in the art, may be substituted at any stage of the syntheses described.

The degree of sweetness of the compounds of the invention is dependent on a number of factors. The most important of these is the nature of the acylating group, R", derived from the carboxylic acid precursor. In general, branched, bulky, hydrophobic groups are preferred, but, more specifically, cycloalkyl and heterocycloalkyl groups containing alkyl substituent groups adjacent to the carbonyl group are preferred. Thus, for example, a cyclopentyl group containing geminal dimethyl substituents in the 2- and 5- positions on the ring is particularly preferred (see Table 1). Substitution in the 3- and 4-positions on the ring does not generally lead to high levels of sweetness.

TABLE 1

Sweetness Data for Gem-Diaminoalkane Derived Sweeteners[a]

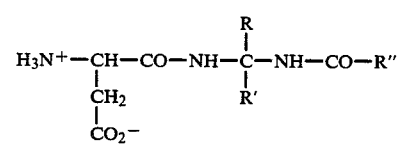

| R | R' | R" | Sweetness[b] |
|---|----|----|--------------|
| CH$_3$ | H | —C(CH$_3$)$_3$ | 75–100 |
| " | " | —C(CH$_3$)$_2$CH$_2$—CH(CH$_3$)$_2$ | 50–75 |
| " | " | H$_3$C-(cyclopropyl) | 10–25 |
| " | " | —CH(cyclopropyl)(cyclopropyl) | 500–700 |

TABLE 1-continued

Sweetness Data for Gem-Diaminoalkane Derived Sweeteners[a]

$$H_3N^+ - CH - CO - NH - \underset{\underset{R'}{|}}{\overset{\overset{R}{|}}{C}} - NH - CO - R''$$
$$\underset{\underset{CO_2^-}{|}}{\overset{|}{CH_2}}$$

| R | R' | R'' | Sweetness[b] |
|---|---|---|---|
| " | " | 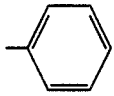 | 5–20 |
| " | " |  | 50–75 |
| " | " | 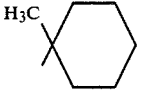 | 35–50 |
| " | " | 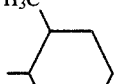 | 150–250 |
| " | " | 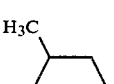 | 150–200 |
| " | " | 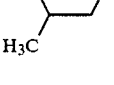 | 150–200 |
| " | " | 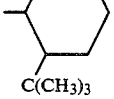 | 75–100 |
| " | " | 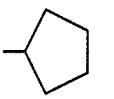 | 300–400 |
| " | " | 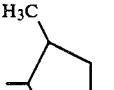 | 800–1000 |
| " | " | " | 600–800[c] |
| CH$_2$CH$_3$ | " | " | 200–300 |
| CH$_2$OH | " | " | 400–500 |
| CH$_3$ | " | 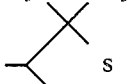 | 150–200 |
| " | " | 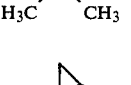 | 75–100 |
| " | " |  | 5–15 |
| " | CH$_3$ |  | 50–100 |

[a]Sweeteners derived from L-aspartyl-R—gem-diaminoalkanes, unless otherwise noted.
[b]Relative to sucrose.
[c]Derived from L-aspartyl-S—1,1-diaminoethane.

A second aspect of the invention relates to the stereochemistry of the two primary chiral centers. The chirality of the first center (aspartic acid or aminomalonic acid) is important. In the case of aspartic acid-containing sweeteners (i.e. I, n=1), it is preferred that the amino acid of the L-configuration be used, although use of racemic (i.e. D,L-) aspartic acid still results in useful sweeteners. However, incorporation of a D-aspartic acid moiety does not lead to useful sweeteners. In the case of aminomalonic acid-containing sweeteners (i.e. I, n=0), the R-enantiomer is preferred, although the racemic, R,S-mixture is most often used in order to avoid the difficult problem of resolution of diastereomers.

The chemistry at the second chiral center (i.e. the gemdiaminoalkane moiety) in the sweeteners is less critical. Thus, while diaminoalkanes of the R-configuration (i.e. those derived from the D-amino acid amides when the sweeteners are synthesized via Scheme 1, or from L-amino acid amides when prepared via Scheme 2) are generally preferred, S-diaminoalkanes may also be used with only minimal loss of sweetness. This result is surprising since in other classes of amino acid-derived sweeteners known in the prior art, chirality at the second center is extremely critical. L-Aspartyl-L-phenylalanine methyl ester, for example, is extremely sweet, while L-aspartyl-D-phenylalanine methyl ester is bitter. This novel discovery is of considerable economic significance since the sweeteners of the present invention may be derived from racemic amino acids, such as alanine, serine, etc., which are much cheaper than their optically pure counterparts. The novel sweeteners of the invention may also be derived from amino acids which are achiral, such as α-aminoisobutyric acid (I, R=R'=CH₃), or from unnatural, optically active amino acids, such as α-methylserine (I, R=CH₂OH, R'=CH₃).

As noted above, a most important, novel aspect of the invention relates to the use of gem-diaminoalkane derivatives for the preparation of useful sweeteners. However, the placement of this diaminoalkane residue in the molecules is also extremely critical. In other words, if the other amide bond in the molecule is reversed to give structures of the type:

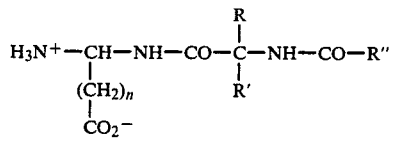

the compounds are not useful as sweeteners.

Thus, the invention is characterized by a number of important features, which include the nature of the substituent group, R'', the inclusion of the diaminoalkane moiety and its position in the molecule and also the stereochemistry of the chiral centers in the molecule. The proper combination of these features provides for optimum sweetness in these molecules.

While the degree of sweetness of the compounds of the invention, as compared to sucrose on a weight to weight basis varies considerably depending upon the substituent R'', all of these compounds provide considerable advantages as sweetening agents due to the fact that the breakdown products thereof are all compatible to the human physiology, e.g. acetic acid and amino acids, and further due to the high stability thereof in both solid form and in solution form. Still further, the compounds of the invention when used with other sweeteners such as saccharine help to avoid the undesired bitter aftertaste of the other sweeteners.

Consequently, the compounds of the invention can be used for the sweetening of edible materials of all types, such as foods, prepared food items, chewing gum, beverages, etc.

The compounds of the invention can be prepared in many forms suitable for use as sweetening agents, such as powders, tablets, granules, solutions, suspensions, syrups, etc.

The invention provides sweetened edible compositions comprising an edible material and a sweetening amount of the compound of the invention either alone or in combination with another sweetening agent such as saccharine. There is actually no limitation as to the edible materials that can be sweetened with the present invention compositions, including fruits, vegetables, juices, meats, egg products, gelatins, jams, jellies, preserves, milk products such as ice cream, sherbert, syrups, beverages such as coffee, tea, carbonated soft drinks, non-carbonated soft drinks, wines, liquors, confections such as candies, etc.

The compounds of the present invention in addition to providing a high degree of sweetness, are of particular interest because these compounds are actually amino acid derivatives rather than peptides. As a consequence, the degree of safety provided by the compounds of the present invention is much greater than with any of the known synthetic sweeteners. Thus, the compounds of the invention are highly stable, do not form diketopiperazines, and the safety of these compounds is implicit in the fact that the compounds are formed from natural amino acids and are formed into stable molecules. Any possible breakdown products of the compounds of the invention are likely to be either easily metabolized or in the pathway of normal ingredients of intermediary metabolism.

Still further, the compounds can be used over a much wider pH range than compounds such as L-aspartyl-L-phenylalanine methyl ester and related dipeptide sweeteners and the compounds also remain stable under conditions of high temperature.

The compounds of the present invention are non-caloric in the amount which would be used for sweetening purposes, are noncariogenic and are safe.

The following examples are given to further illustrate the present invention. The scope of the invention is not, however, meant to be limited to the specific details of the examples:

EXAMPLE 1

N-(L-Aspartyl)-N'-Cyclopentanecarbonyl-R-1,1-Diaminoethane

[Formula I, R=CH₃, R'=H, R''=cyclopentyl]

A. D-Alanine (20 g, 0.225 mole) was dissolved in dimethylformamide (400 ml), treated with chlorotrimethylsilane (26.8 g, 0.250 mole) and the mixture stirred at room temperature until a homogeneous solution was obtained (approx. 45 minutes). Meanwhile, N^α-benzyloxycarbonyl-β-benzyl-L-aspartic acid (72 g, 0.200 mole) was dissolved in a 1:1 mixture of dimethylformamide and tetrahydrofuran (880 ml), cooled to a −15° C. and treated with N-methylmorpholine (22.4 ml, 0.200 mole) and isobutyl chloroformate (26.2 ml, 0.200 mole). After 8 minutes' activation at −15° C. the precooled solution of D-alanine silyl ester from above was added, followed by the dropwise addition of N-methylmorpholine (22.4 ml, 0.200 mole), ensuring that the temperature of the reaction mixture was maintained at −15° C. The solution was allowed to warm to room temperature slowly and stirred for several hours before acidifying to pH 1-2 (with cooling) using aqueous hydrochloric acid. Chloroform was added, the phases separated and the aqueous layer re-extracted with chloroform. The combined organic extracts were washed with 1N hydrochloric acid (3×), saturated aqueous sodium chloride and dried (MgSO₄). After evaporation of the solvent under reduced pressure, the oily residue was triturated with ether. The resulting solid was filtered and dried in vacuo to give N^α-benzyloxycarbonyl-β-benzyl-L-aspartyl-D-alanine (67 g), m.p. 158°–159° C., which was homogeneous by TLC.

B. The product from Part A (64 g, 0.150 mole) was dissolved in dimethylformamide (600 ml), cooled to −15° C. and treated with N-methylmorpholine (16.5 ml, 0.150 mole) and isobutyl chloroformate (19.5 ml, 0.150 mole). After 5 minutes' activation at −15° C., 1-hydroxybenzotriazole ammonium salt (34 g, 0.225 mole) was added as a solid, and the mixture stirred at −15° C. for 15 minutes. After warming slowly to room temperature over 4 hours, chloroform and water were added, the phases separated and the aqueous phase reextracted with chloroform. The combined organic extracts were washed with 1N hydrochloric acid (3×), saturated aqueous sodium bicarbonate (3×), saturated sodium chloride and dried (MgSO₄). The solvent was evaporated under reduced pressure and the solid residue recrystallized from ethyl acetate/hexanes to give N$^\alpha$-benzyloxycarbonyl-$\beta$-benzyl-L-aspartyl-D-alanyl amide (50 g), m.p. 170°-171° C., which was homogeneous by TLC.

C. The product from Part B (2.2 g, 5.1 mmole) was dissolved in acetonitrile (50 ml) and the solution diluted with an equal volume of water. Iodobenzene bis(trifluoroacetate) (2.4 g, 5.6 mmole) was then added and the reaction mixture stirred at room temperature for 4 hours (clear solution after approximately 2 hours). The solution was evaporated and the residue redissolved in aqueous HCl and lyophilized, to give N-(N$^\alpha$-benzyloxycarbonyl-$\beta$-benzyl-L-aspartyl)-R-1,1-diaminoethane hydrochloride in quantitative yield, which was used without further purification.

D. The product from Part C, (2.95 g, 5.1 mmole) was dissolved in tetrahydrofuran (50 ml), cyclopentanecarbonyl chloride (1.5 g, 10.6 mmole) added, followed by potassium bicarbonate (2.5 g, 25 mmole) and water (50 ml) and the mixture stirred at room temperature. After 2.5 hours, a clear solution was obtained but TLC indicated that reaction was incomplete and second portions of cyclopentanecarbonyl chloride (1.5 g, 10.6 mmole) and potassium bicarbonate (2 g, 20 mmole) were therefore added. The process was repeated 15 minutes later. After 20 minutes, ethyl acetate and water were added, the phases separated and the aqueous phase extracted with ethyl acetate. The combined organic phases were washed with 1M sodium bicarbonate (2×), 2N hydrochloric acid (3×), again with 1M sodium bicarbonate (2×) and finally with saturated sodium chloride and dried (MgSO$_4$). The solution was filtered, evaporated under reduced pressure and the residue triturated with ether to provide N-(N$^\alpha$-benzyloxycarbonyl-$\beta$-benzyl-L-aspartyl)-N'-cyclopentanecarbonyl-R-1,1-diaminoethane (1.5 g) as a crystalline solid which was homogeneous by TLC. The nmr spectrum of the product was consistent with the assigned structure.

E. The product from Part D (1.5 g, 3.03 mmole) was hydrogenated in glacial acetic acid (50 ml) over 10% palladium on carbon (approx. 0.2 g) at 40 p.s.i. overnight. The catalyst was filtered, washed with glacial acetic acid and the filtrate lyophilized. The resultant powder was redissolved in water and relyophilized (twice) to give N-(L-aspartyl)-N'-cyclopentanecarbonyl-1,1-diaminoethane in quantitative yield, m.p. 220° C. dec.

Sweetness = 75–100 × sucrose.

EXAMPLE 2

N-(L-Aspartyl)-N'-Trimethylacetyl-R-1,1-Diaminoethane

[Formula I, R=CH$_3$, R'=H, R"=C(CH$_3$)$_3$]

A. N-(N$^\alpha$-Benzyloxycarbonyl-$\beta$-benzyl-L-aspartyl)-R-1,1-diaminoethane hydrochloride (5.2 g, 12 mmole), prepared as described in Example 1, Part C, was suspended in water (50 ml) at room temperature. Potassium bicarbonate (6 g, 60 mmole) was added, followed by pivaloyl chloride (1.5 ml, 12 mmole) dissolved in acetonitrile (50 ml). The homogeneous reaction mixture was stirred at room temperature for 3 hours when TLC showed incomplete reaction. Further aliquots of the acid chloride (0.8 ml) and potassium bicarbonate (5 g) were therefore added and the reaction mixture stirred for a further 1 hour. The solution was then diluted with ethyl acetate (500 ml) and extracted with 1N hydrochloric acid (3×), saturated aqueous sodium bicarbonate (3×) and saturated sodium chloride (1×). The organic phase was dried (MgSO$_4$), filtered and evaporated to dryness under reduced pressure. The residue was crystallized from ethyl acetate/hexanes to provide N-(N$^\alpha$-benzyloxycarbonyl-$\beta$-benzyl-L-aspartyl)-N'-trimethylacetyl-R-1,1-diaminoethane (4.8 g) which was homogeneous by TLC, m.p. 66°-69° C. The nmr spectrum of the product was consistent with the assigned structure.

B. The product from Part A (4 g) was dissolved in glacial acetic acid (150 ml) and hydrogenated overnight at 40 p.s.i. over 10% palladium on carbon (approx. 0.5 g). The catalyst was filtered, washed with glacial acetic acid and the filtrate lyophilized. The resultant powder was redissolved in water and relyophilized (twice) to give N-(L-aspartyl)-N'-trimethylacetyl-R-1,1-diaminoethane in quantitative yield, m.p. 150° C.

Sweetness = 75–100 × sucrose

EXAMPLE 3

N-(L-Aspartyl)-N'-Cyclohexanecarbonyl-R-1,1-Diaminoethane

[Formula I, R=CH$_3$, R'=H, R"=cyclohexyl]

A. N-(N$^\alpha$-Benzyloxycarbonyl-$\beta$-benzyl-L-aspartyl)-R-1,1-diaminoethane hydrochloride (Example 1, Part C) (5.2 g, 12 mmole) was treated with cyclohexanecarbonyl chloride (1.75 ml, 12 mmole) and potassium bicarbonate (6 g, 60 mmole), as described in Example 2, Part A. A second aliquot of the acid chloride (0.8 ml) and potassium bicarbonate (5 g) were added after 3 hours. The product precipitated and was collected by filtration, dried, triturated with hexane and dried in vacuo to give N-(N$^\alpha$-benzyloxycarbonyl-$\beta$-benzyl-L-aspartyl)-N'-cyclohexanecarbonyl-R-1,1-diaminoethane (5.8 g) which was homogeneous by TLC, m.p. 178°-180° C. The nmr spectrum of the product was consistent with the assigned structure.

B. The product from Part A (5 g) was hydrogenated in the usual manner in glacial acetic acid (150 ml) over palladium on carbon. After lyophilization several times from water, N-(L-aspartyl)-N'-cyclohexanecarbonyl-R-1,1-diaminoethane was obtained in quantitative yield.

Sweetness = 50–75 × sucrose.

EXAMPLE 4

N-(L-Aspartyl)-N'-Benzoyl-R-1,1-Diaminoethane

[Formula I, R=CH$_3$, R'=H, R"=phenyl]

A. N-(N$^\alpha$-Benzyloxycarbonyl-$\beta$-benzyl-L-aspartyl)-R-1,1-diaminoethane hydrochloride (Example 1, Part C) (5.2 g, 12 mmole) was dissolved in tetrahydrofuran (100 ml) at room temperature. Triethylamine (1.68 ml, 12 mmole) was added, followed by benzoyl chloride (1.62 g, 12 mmole) and a second equivalent of triethylamine (1.68 ml) and the mixture stirred at room temperature. After 3 hours reaction was incomplete by TLC and another aliquot of triethylamine (1.15 ml) was therefore added and the mixture stirred at room temperature for a further 1 hour. The reaction mixture was then evaporated to dryness, the residue redissolved in ethyl acetate (approx. 1000 ml), and extracted in the usual manner. (This procedure proved to be difficult because of the formation of emulsions and precipitates.) After drying (MgSO$_4$) the organic phase was evaporated to dryness under reduced pressure and the residue crystallized from ethyl acetate/hexanes to give N-(N$^\alpha$-benzyloxycarbonyl-$\beta$-benzyl-L-aspartyl)-N'-benzoyl-R-1,1-diaminoethane (1.5 g) which was homogeneous by TLC. The nmr spectrum of the product was consistent with the assigned structure.

B. The product from Part A (1 g) was hydrogenated in the usual manner in glacial acetic acid (50 ml) over 10% palladium on carbon. Lyophilization several times from water gave N-(L-aspartyl)-N'-benzoyl-R-1,1-diaminoethane in quantitative yield.

Sweetness = 5–20 × sucrose.

EXAMPLE 5

N-(L-Aspartyl)-N'-(2-Norbornanecarbonyl)-R-1,1-Diaminoethane

[Formula I, R=CH$_3$, R'=H, R"=2-norbornyl]

A. N$^\alpha$-Benzyloxycarbonyl-$\beta$-benzyl-L-aspartyl-D-alanyl amide (Example 1, Part B) (10.7 g, 25 mmole) was suspended in 1:1 acetonitrile:water (200 ml) and iodobenzene bis(trifluoroacetate) (12 g, 28 mmole) added. The reaction mixture was stirred at room temperature for 4 hours (a homogeneous solution was obtained after 2 hours) and then treated with norbornane-2-carboxyl chloride (10 g, 63 mmole) and potassium bicarbonate (12 g, 120 mmole). After stirring for 2 hours at room temperature, TLC showed complete reaction and the product was extracted and worked up in the usual manner. After drying (MgSO$_4$), the organic phase was evaporated to dryness under reduced pressure and the residue crystallized from ethyl acetate/hexanes to give N-(N$^\alpha$-benzyloxycarbonyl-$\beta$-benzyl-L-aspartyl)-N'-(2-norbornanecarbonyl)-R-1,1-diaminoethane (10.3 g), m.p. 127°–130° C., which was homogeneous by TLC. The nmr spectrum of the product was consistent with the assigned structure.

B. The product from Part A (9 g) was hydrogenated in the usual manner in glacial acetic acid (200 ml) over 10% palladium on carbon. After lyophilization several times from water, N-(L-aspartyl)-N'-(2-norbornanecarbonyl)-R-1,1-diaminoethane was obtained in quantitative yield, m.p. 177°–178° C.

Sweetness = 75–100 × sucrose.

EXAMPLE 6

N-(L-Aspartyl)-N'-(1-Adamantanecarbonyl)-R-1,1-Diaminoethane

[Formula I, R=CH$_3$, R'=H, R"=1-adamantyl]

A. N$^\alpha$-Benzyloxycarbonyl-$\beta$-benzyl-L-aspartyl-D-alanyl amide (Example 1, Part B) (8.54 g, 20 mmole) was treated with iodobenzene bis(trifluoroacetate) using the procedure described in Example 5, Part A. The resulting solution was treated with 1-adamantanecarbonyl chloride (6 g, 30 mmole) and potassium bicarbonate (15 g, 150 mmole) and stirred at room temperature for 4 hours. After the usual workup, the crude product was obtained as an oil which was purified by chromatography on silica gel, eluting with chloroform:hexane (3:1, v/v). N-(N$^\alpha$-benzyloxycarbonyl-$\beta$-benzyl-L-aspartyl)-N'-(1-adamantanecarbonyl)-R-1,1-diaminoethane was obtained as an oil (2.5 g) which was homogeneous by TLC. The nmr spectrum of the product was consistent with the assigned structure.

B. The product from Part A (2.0 g) was hydrogenated in the usual manner in glacial acetic (50 ml) over 10% palladium on carbon. After lyophilization several times from water, N-(L-aspartyl)-N'-(1-adamantanecarbonyl)-R-1,1-diaminoethane was obtained in quantitative yield, m.p. 174°–175° C.

Sweetness = 5–15 × sucrose.

EXAMPLE 7

N-(L-Aspartyl)-N'-(2-Methylcyclohexanecarbonyl)-R-1,1-Diaminoethane

[Formula I, R=CH$_3$, R'=H, R"=2-methylcyclohexyl]

A. Ethyl 2-methylcyclohexanecarboxylate (50 g, 0.295 mmole) was added to a solution of potassium hydroxide (27 g, 0.48 mole) in anhydrous methanol (300 ml). The mixture was stirred overnight at room temperature and then evaporated to dryness under reduced pressure. The residue was redissolved in water and the solution extracted with ether (3×200 ml), then acidified (pH<2), and re-extracted with ether (3×200 ml). The final, combined organic extracts were washed with water, dried (MgSO$_4$) and evaporated under reduced pressure to yield 2-methylcyclohexanecarboxylic acid. The crude product was converted to the acid chloride by treatment with excess thionyl chloride (100 ml) at room temperature for 30 minutes. The thionyl chloride was evaporated under reduced pressure and the residue distilled in vacuo to give 2-methylcyclohexanecarboxyl chloride (33 g).

B. N$^\alpha$-Benzyloxycarbonyl-$\beta$-benzyl-L-aspartyl-D-alanyl amide (Example 1, Part B) (10.7 g, 25 mmole) was treated with iodobenzene bis(trifluoroacetate) using the procedure described in Example 5, Part A. The resulting solution was treated with potassium bicarbonate (20 g, 200 mmole), followed by 2-methylcyclohexanecarboxyl chloride (5.5 g, 35 mmole). The reaction was followed by TLC. Addition of two further aliquots (3 g each) of the acid chloride was required for complete reaction. The reaction mixture was worked up in the usual manner and the product crystallized from ethyl acetate/hexanes (yield=10.0 g) and then chromatographed on silica gel, eluting with 5% methanol in chloroform, to give N-(N$^\alpha$-benzyloxycarbonyl-$\beta$-benzyl-L-aspartyl)-N'-(2-methylcyclohexanecarbonyl)-R-1,1-diaminoethane (8.0 g) which was homogeneous by TLC. The nmr spectrum of the product was consistent with the assigned structure.

C. The product from Part B (8.0 g) was hydrogenated in the usual manner in glacial acetic acid (200 ml) over 10% palladium on carbon. After lyophilization from water several times N-(L-aspartyl)-N'-(2-methylcyclohexanecarbonyl)-R-1,1-diaminoethane was obtained in quantitative yield, m.p. 203°–204° C.

Sweetness = 150–250 × sucrose.

EXAMPLE 8

N-(L-Aspartyl)-N'-(1-Methylcyclohexanecarbonyl)-R-1,1-Diaminoethane

[Formula I, R=CH$_3$, R'=H, R"=1-methylcyclohexyl]

A. 1-Methylcyclohexanecarboxylic acid (50 g, 350 mmole) was converted to the acid chloride by treatment with an excess of thionyl chloride (75 ml) at room temperature. The excess thionyl chloride was evaporated under reduced pressure and the residue distilled in vacuo to provide 1-methylcyclohexanecarboxyl chloride (49 g).

B. $N^\alpha$-Benzyloxycarbonyl-$\beta$-benzyl-L-aspartyl-D-alanyl amide (Example 1, Part B) (10.7 g, 25 mmole) was treated with iodobenzene bix(trifluoroacetate) using the procedure described in Example 5, Part A. The resulting solution was treated with potassium bicarbonate (20 g, 200 mmole), followed by 1-methylcyclohexanecarboxyl chloride (5.5 g, 35 mmole), and two further aliquots (3 g each) over 3 hours. When reaction was complete by TLC, the reaction mixture was worked up in the usual manner and the crude product purified by chromatography on silica gel, eluting with 5% methanol in chloroform to give N-($N^\alpha$-benzyloxycarbonyl-$\beta$-benzyl-L-aspartyl)-N'-(1-methylcyclohexanecarbonyl)-R-1,1-diaminoethane (8.2 g) which was homogeneous by TLC. The nmr spectrum of the product was consistent with the assigned structure.

C. The product from Part B (8.2 g) was hydrogenated in the usual manner in glacial acetic acid (200 ml) over 10% palladium on carbon. After lyophilization several times from water, N-(L-aspartyl)-N'-(1-methylcyclohexanecarbonyl)-R-1,1-diaminoethane was obtained in quantitative yield, m.p. 142°–143° C.

Sweetness = 35–50 × sucrose.

EXAMPLE 9

N-(L-Aspartyl)-N'-(1-Methylcyclopropanecarbonyl)-R-1,1-Diaminoethane

[Formula I, R=CH$_3$, R'=H,
R"=1-methylcyclopropyl]

A. $N^\alpha$-Benzyloxycarbonyl-$\beta$-benzyl-L-aspartyl-D-alanyl amide (Example 1, Part B) (10.7 g, 25 mmole) was treated with iodobenzene bis(trifluoroacetate) using the procedure described in Example 5, Part A. The resulting solution was treated with potassium bicarbonate (20 g, 200 mmole), followed by 1-methylcyclopropanecarboxyl chloride (3.65 g, 35 mmole), and two further aliquots (2 g each) over 3 hours. When reaction was complete by TLC the reaction mixture was worked up in the usual manner and the product crystallized from ethyl acetate/hexanes to give N-($N^\alpha$-benzyloxycarbonyl-$\beta$-benzyl-L-aspartyl)-N'-(1-methylcyclopropanecarbonyl)-R-1,1-diaminoethane (8 g) which was homogeneous by TLC, m.p. 120°–123° C. The nmr spectrum of the product was consistent with the assigned structure.

B. The product from Part A (7 g) was hydrogenated in the usual manner in glacial acetic acid (200 ml) over 10% palladium on carbon. After lyophilization from water several times N-(L-aspartyl)-N'-(1-methylcyclopropanecarbonyl)-R-1,1-diaminoethane was obtained in quantitative yield, m.p. 134°–135° C.

Sweetness = 10–25 × sucrose.

EXAMPLE 10

N-(L-Aspartyl)-N'-(2,2,4-trimethylpentanoyl)-R-1,1-Diaminoethane

[Formula I, R=CH$_3$, R'=H,
R"=1,1,3-trimethylbutyl]

A. 2,4-Dimethyl-3-pentanol (29 g, 0.25 mole), dissolved in formic acid (98%, 46 g, 1 mole), was added dropwise over one hour to a rapidly-stirred, ice-cooled mixture of formic acid (98%, 3 ml) and concentrated sulfuric acid (270 ml). During the addition the reaction mixture foamed vigorously and was stirred for a further one hour at 10°–20° C. The mixture was poured on to ice (1 kg) and the resulting solution extracted with hexanes (3×200 ml). The combined organic phases were extracted with 2N potassium hydroxide (2×200 ml) plus ice (50 g) and the aqueous extracts washed with hexanes (100 ml). The aqueous phase was then acidified (pH 2) and the product extracted into hexanes (3×200 ml). After washing with saturated sodium chloride and drying (MgSO$_4$), the solution was evaporated under reduced pressure and the residue distilled to give 2,2,4-trimethylpentanoic acid (36 g).

B. The product from Part A (36 g) was treated with an excess of thionyl chloride (50 ml) and the mixture stirred at room temperature overnight. The thionyl chloride was evaporated under reduced pressure and the product distilled in vacuo to give 2,2,4-trimethylpentanoyl chloride (35 g).

C. $N^\alpha$-Benzyloxycarbonyl-$\beta$-benzyl-L-aspartyl-D-alanyl amide (Example 1, Part B) (10.7 g, 25 mmole) was treated with iodobenzene bis(trifluoroacetate) using the procedure described in Example 5, Part A. The resulting solution was treated with potassium bicarbonate (20 g, 200 mmole) followed by 2,2,4-trimethylpentanoyl chloride (5.4 g, 30 mmole) and a second portion (2.7 g, 15 mmole) after 30 minutes. The reaction mixture was stirred at room temperature for a further 1.5 hours, when reaction was completed by TLC. The reaction mixture was worked up in the usual manner and the product crystallized from ethyl acetate/hexanes to give N-($N^\alpha$-benzyloxycarbonyl-$\beta$-benzyl-L-aspartyl)-N'-(2,2,4-trimethylpentanoyl)-R-1,1-diaminoethane (9.4 g), which was homogeneous by TLC, m.p. 98°–101° C. The nmr spectrum of the product was consistent with the assigned structure.

D. The product from Part C (9.0 g) was hydrogenated in the usual manner in glacial acetic acid (200 ml) over 10% palladium on carbon. After lyophilization from water several times N-(L-aspartyl)-N'-(2,2,4-trimethylpentanoyl)-1,1-diaminoethane was obtained in quantitative yield, m.p. 120° C. dec.

Sweetness = 50–75 × sucrose.

EXAMPLE 11

N-(L-Aspartyl)-N'-(Trimethylcyclohexanecarbonyl)-R-1,1-Diaminoethane

[Formula I, R=CH$_3$, R'=H,
R"=trimethylcyclohexyl]

A. A solution of 2,6-dimethylcyclohexanone (35 g, 0.277 mole) in ether (200 ml) was cooled to −78° C. and treated with a 2-fold excess of a solution of methyl magnesium bromide in ether (2.8M, 198 ml). After stirring at −78° C. for 3 hours the reaction mixture was warmed to 0° C. and quenched carefully with water and brine. The organic layer was separated, dried (MgSO$_4$) and the ether evaporated under reduced pressure to give 1,2,6-trimethylcyclohexanol (32.2 g).

B. A solution of 1,2,6-trimethylcyclohexanol (32.2 g, 0.226 mole) in formic acid (98%, 46 g, 1 mole) was added dropwise to an ice-cooled mixture of formic acid (90%, 3 ml) and sulfuric acid (90%, 270 ml, 4.86 mole). The solution foamed vigorously during the addition. After stirring for a further one hour the reaction mixture was poured on to crushed ice (2 kg) and worked up as described for Example 10, Part A. Yield of trimethylcyclohexanecarboxylic acid was 29.9 g.

C. The product from Part B (29.9 g, 0.176 mole) was added carefully to excess thionyl chloride (65 ml) and the mixture stirred at room temperature overnight. The thionyl chloride was evaporated under reduced pressure to give trimethylcyclohexanecarboxyl chloride (25.5 g) which was used without further purification.

D. $N^\alpha$-Benzyloxycarbonyl-$\beta$-benzyl-L-aspartyl-D-alanyl amide (Example 1, Part B) (10.7 g, 25 mmole) was treated with iodobenzene bis(trifluoroacetate) using the procedure described in Example 5, Part A. The resulting solution was treated with potassium bicarbonate (20 g, 200 mmole) and trimethylcyclohexanecarboxyl chloride (6.15 g, 30 mmole), followed by a second portion (3 g) after 30 minutes. After 3 hours, when TLC showed that the reaction was complete, the reaction mixture was worked up in the usual manner. The product was crystallized from ethyl acetate/hexanes to give N-($N^\alpha$-benzyloxycarbonyl-$\beta$-benzyl-L-aspartyl)-N'-(trimethylcyclohexanecarbonyl)-R-1,1-diaminoethane (8.6 g) which was homogeneous by TLC. The nmr spectrum of the product was consistent with the assigned structure.

E. The product from Part D (8 g) was hydrogenated in the usual manner in glacial acetic acid (200 ml) over 10% palladium on carbon. After lyophilization from water several times N-(L-aspartyl)-N'-trimethylcyclohexanecarbonyl-R-1,1-diaminoethane was obtained in quantitative yield.

Sweetness = 25–50 × sucrose.

EXAMPLE 12

N-(L-Aspartyl)-N'-(1,1-Dicyclopropylacetyl)-R-1,1-Diaminoethane

[Formula I, R=CH$_3$, R'=H,
R''=dicyclopropylmethyl]

A. Methyltriphenylphosphonium bromide (116 g, 0.325 mole) was suspended in dry ether (600 ml), cooled to $-10°$ C. and treated with a solution of n-butyllithium in hexane (2.2M, 175 ml). The mixture was stirred for 5 minutes before adding a solution of dicyclopropyl ketone (35.6 g, 0.325 mole) in ether (100 ml) which had been precooled to 0° C. The suspension was allowed to warm to room temperature and then stirred for a further 2 hours. Water (1000 ml) was then added, in small portions at first, and the mixture stirred until the precipitate dissolved. The organic layer was separated, washed with water, dried (MgSO$_4$) and the solvent evaporated under reduced pressure. The residue contained a solid (triphenylphosphine oxide) which was separated from the oil, washed with a little ether and the combined etheral/organic residues were fractionated to yield dicyclopropyl ethylene (6.5 g), b.p. 130° C./760 mm, which was pure by GC.

B. Dicyclopropyl ethylene (19 g, 0.176 mole) was dissolved in dry tetrahydrofuran (100 ml) in a three-neck flask under nitrogen and treated with borane-tetrahydrofuran in tetrahydrofuran (1M, 210 ml). The mixture was stirred at room temperature for 4 hours before adding cautiously (foaming occurs) 3N sodium hydroxide (60 ml). After addition was complete, aqueous hydrogen peroxide (30%, 60 ml) was added dropwise at a rate sufficient to maintain reflux. When addition was complete, the mixture was refluxed for a further 30 minutes, cooled and the aqueous layer saturated with sodium chloride. The layers were separated, the organic layer dried (MgSO$_4$) and evaporated under reduced pressure to give a quantitative yield of 2,2-dicyclopropylethanol which was pure by GC. (The product could also be distilled, b.p. 99° C./25 mm.)

C. The product from Part B (16 g, 0.127 mole) was dissolved in ether (300 ml) and the solution added to a mixture of potassium dichromate (60 g) dissolved in concentrated sulfuric acid (120 ml) and ice-water (600 ml). The reaction mixture, which immediately became dark, was stirred at room temperature for one hour. The organic layer was then separated, washed with water (3×), dried (MgSO$_4$) and the ether evaporated under reduced pressure. The residue was distilled to give 1,1-dicyclopropylacetic acid (10.3 g), b.p. 130°–141° C./25 mm, which was pure by GC.

D. The product from Part C (10 g, 0.071 mole) was dissolved in dry tetrahydrofuran (25 ml) and treated with excess thionyl chloride (25 ml). After stirring the mixture at room temperature for one hour, conversion to the acid chloride was complete by GC. The solvent and excess thionyl chloride were evaporated under reduced pressure to give 1,1-dicyclopropylacetyl chloride in quantitative yield, which was used without further purification.

E. $N^\alpha$-Benzyloxycarbonyl-$\beta$-benzyl-L-aspartyl-D-alanyl amide (Example 1, Part B) (8.54 g, 20 mmole) was treated with iodobenzene bis(trifluoroacetate) using the procedure described in Example 5, Part A. The resulting solution was treated with potassium bicarbonate (16 g, 160 mmole), followed by dropwise addition of 1,1-dicyclopropylacetyl chloride (4.7 g, 30 mmole). A precipitate formed almost immediately and the reaction mixture was stirred at room temperature for one hour. Water and chloroform were then added, the phases separated and the organic layer washed with saturated aqueous sodium bicarbonate (3×), 3N aqueous hydrochloric acid and saturated sodium chloride. After drying (Na$_2$SO$_4$) the solvent was evaporated under reduced pressure and the solid residue recrystallized from ethyl acetate to give N-($N^\alpha$-benzyloxycarbonyl-$\beta$-benzyl-L-aspartyl)-N'-(1,1-dicyclopropylacetyl)-R-1,1-diaminoethane (6.5 g), which was homogeneous by TLC, m.p. 200°–201° C. The nmr spectrum of the product was consistent with the assigned structure.

F. The product from Part E (4 g) was hydrogenated in the usual manner in glacial acetic acid (200 ml) over 10% palladium on charcoal. After lyophilization several times from water, the residue was crystallized from ethanol/water to give N-(L-aspartyl)-N'-(1,1-dicyclopropylacetyl)-R-1,1-diaminoethane (1.0 g), m.p. 209°–210° C.

Sweetness = 500–700 × sucrose.

EXAMPLE 13

N-(L-Aspartyl)-N'-(2,5-Dimethylcyclopentanecarbonyl)-R-1,1-Diaminoethane

[Formula I, R=CH$_3$, R'=H,
R''=2,5-dimethylcyclopentyl]

A. Sodium metal (16 g, 0.7 mole) was dissolved in absolute ethanol (500 ml) under argon with cooling as necessary to maintain a temperature of <70° C. The solution was cooled and redistilled diethyl malonate (54.3 g, 0.362 mole) was added dropwise, with cooling as necessary, followed by 2,5-dibromohexane (85 g, 0.348 mole) in a single portion. The reaction mixture was stirred overnight at room temperature and then refluxed for 2 hours. The mixture was then concentrated to approximately half the volume under reduced pressure, water (500 ml) added and the mixture extracted with ether (3×200 ml). The combined extracts were dried (Na$_2$SO$_4$), filtered, and evaporated under reduced pressure. The residue was fractionated in vacuo to yield diethyl 2,5-dimethylcyclopentane-1,1-dicarboxylate (35 g), which was homogeneous by GC.

B. The product from Part A (35 g, 0.145 mole) was added to a solution of potassium hydroxide (55 g) in absolute ethanol (300 ml) and the mixture refluxed overnight. The reaction mixture was evaporated under reduced pressure and the residue dissolved in water (500 ml). The aqueous solution was extracted with ethyl acetate (200 ml), acidified to pH 1 (conc. HCl) and extracted with ether (3×200 ml). The combined extracts were washed with 1N hydrochlorid acid and dried (Na$_2$SO$_4$). The solution was evaporated under reduced pressure and the residual oil triturated with pentane to induce crystallization. The product was filtered and dried in vacuo to give 2,5-dimethylcyclopentane-1,1-dicarboxylic acid (10.5 g) which was homogeneous by GC.

C. The product from Part B (10.5 g, 56 mmole) was heated to 230° C. in a stream of argon for 1.25 hour. The residue was dissolved in tetrahydrofuran, decolorized (Norit A), and the solvent evaporated under reduced pressure. The residual oil crystallized on standing to give 2,5-dimethylcyclopentanecarboxylic acid (6.3 g), m.p. 45° C., which was pure by GC.

D. The product from Part C (6.3 g, 48 mmole) was dissolved in tetrahylrofuran/thionyl chloride (1:1, v/v; 100 ml) and the mixture stirred at room temperature for one hour. The solution was evaporated under reduced pressure to give a quantitative yield of 2,5-dimethylcyclopentanecarbonyl chloride which was used without further purification.

E. N$^\alpha$-Benzyloxycarbonyl-$\beta$-benzyl-L-aspartyl-D-alanyl amide (Example 1, Part B) (8.6 g, 20 mmole) was treated with iodobenzene bis(trifluoroacetate) using the procedure described in Example 5, Part A. The resulting solution was treated with potassium bicarbonate (20 g, 200 mmole), followed by 2,5-dimethylcyclopentanecarboxyl chloride (4.8 g, 30 mmole), added dropwise over 5 minutes. The product precipitated almost immediately and stirring was continued for a further 2 hours at room temperature. The reaction mixture was worked up in the usual manner, except that the product crystallized during the drying of the final extracts over Na$_2$SO$_4$. The solution was therefore heated to boiling, filtered hot and the Na$_2$SO$_4$ washed with ethyl acetate. The filtrate was evaporated under reduced pressure and the residue crystallized from ethyl acetate/hexanes to give N-(N$^\alpha$-benzyloxycarbonyl-$\beta$-benzyl-L-aspartyl)-N'-(2,5-dimethylcyclopentanecarbonyl)-1,1-diaminoethane, (6.1 g) which was homogeneous by TLC, m.p. 193°–195° C. The nmr spectrum of the product was consistent with the assigned structure.

F. The product from Part E (5.5 g) was hydrogenated in the usual manner in glacial acetic acid (200 ml) over 10% palladium on carbon. After lyophilization several times from water, the solid residue was recrystallized from ethanol/water to give N-(L-aspartyl)-N'-(2,5-dimethylcyclopentanecarbonyl)-R-1,1-diaminoethane (2.6 g), m.p. 208°–209° C.

Sweetness = 300–400 × sucrose.

EXAMPLE 14

N-(L-Aspartyl)-N'-(2,2,5,5-Tetramethylcyclopentanecarbonyl)-R-1,1-Diaminoethane

[Formula I, R=CH$_3$, R'=H, R''=2,2,5,5-tetramethylcyclopentyl]

A. Sodium hydride (50% dispersion in oil; 144 g, 3.0 mole) was added to a 3-liter, 3-neck flask fitted with a reflux condenser, a mechanical stirrer and a nitrogen inlet. A moderate stream of nitrogen was passed through the flask and dry tetrahydrofuran (1.5 l) added. Solutions of cyclopentanone (53.6 g, 0.64 mole) in dry tetrahydrofuran (350 ml) and dimethyl sulfate (285 ml, 3.0 mole) in the same solvent (120 ml) were added simultaneously in small portions (20–40 ml) to the stirred suspension, so as to maintain a gentle evolution of hydrogen. The reaction mixture was cooled as necessary to maintain a temperature of <40° C. When addition was complete (several hours) the reaction mixture was refluxed for 2 hours. After cooling, t-butanol (100 ml) was added slowly to destroy excess hydride, followed by water (1 l), cautiously at first. The reaction mixture was then refluxed 2 hours to destroy excess dimethyl sulfate. On cooling, the layers were separated and the organic phase washed with saturated sodium chloride and dried (Na$_2$SO$_4$). The solvent was evaporated under reduced pressure and the residue fractionated in vacuo to give 2,2,5,5-tetramethylcyclopentanone (59 g), b.p. 55° C./20 mm.

B. A solution of 2,2,5,5-tetramethylcyclopentanone (30 g, 0.215 mole) in ether (50 ml) was treated, under nitrogen, with a 3M solution of methyl magnesium bromide in ether (100 ml). The reaction mixture was stirred overnight at room temperature and saturated aqueous ammonium chloride (65 ml) then added dropwise. The mixture was stirred for 10 minutes, the ether solution decanted and the solid residue triturated with ether. The ether extracts were dried (Na$_2$SO$_4$) and evaporated under reduced pressure to give crude 1,2,2,5,5-pentamethylcyclopentanol (30 g) which was used without further purification.

C. The crude product from Part B (30 g) was dissolved in pyridine (150 ml), the solution cooled to 0° C. and treated (dropwise) with thionyl chloride (20 ml, 0.28 mole), maintaining a temperature of <5° C. The reaction mixture was stirred overnight, filtered and ether and water added. The phases were separated and the organic phase washed with water (2×200 ml) and dried (Na$_2$SO$_4$). The solvent was evaporated under reduced pressure to give 1-methylene-2,2,5,5-tetramethylcyclopentane (10.8 g) which was pure by GC.

D. The product from Part C (10.8 g, 78 mmole) was dissolved in dry tetrahydrofuran (100 ml) and treated under nitrogen with 1M borane-tetrahydrofuran in tetrahydrofuran (100 ml). The reaction mixture was stirred overnight at room temperature and treated with 3N aqueous sodium hydroxide (40 ml), followed by dropwise addition of 30% aqueous hydrogen peroxide (40 ml) at a rate sufficient to maintain a gentle reflux. The mixture was refluxed for a further one hour, sodium chloride added to saturation, and the mixture cooled to room temperature with stirring. The phases were separated, the organic phase dried (Na$_2$SO$_4$) and evaporated under reduced pressure to give a quantitative yield of crude 2,2,5,5-tetramethylcyclopentylmethanol which was used without further purification.

E. The product from Part D was dissolved in ether (300 ml) and added to a solution of potassium dichromate (45 g, 0.15 mole) in concentrated sulfuric acid (90 ml, 1.7 mole) and water (450 ml). The mixture was stirred at room temperature for 3 hours. The phases were then separated, the organic phase washed with saturated sodium chloride and dried (Na$_2$SO$_4$). The solvent was evaporated under reduced pressure and the residue distilled in vacuo to give 2,2,5,5-tetramethylcyclopentanecarboxylic acid (6.6 g) which was homogeneous by GC.

F. The product from Part E (6.5 g, 38 mmole) was dissolved in tetrahydrofuran (100 ml) and treated dropwise with excess thionyl chloride (20 ml, 270 mmole). The solution was refluxed for two hours, evaporated under reduced pressure and the residue distilled in vacuo to give 2,2,5,5-tetramethylcyclopentanecarboxyl chloride (4.8 g), b.p. 65°–75° C./4 mm.

G. N$^\alpha$-Benzyloxycarbonyl-$\beta$-benzyl-L-aspartyl-D-alanyl amide (Example 1, Part B) (10.7 g, 25 mmole) was treated with iodobenzene bis(trifluoroacetate) as described in Example 5, Part A. The resulting solution was evaporated to near dryness under reduced pressure, water and a large excess of concentrated hydrochloric acid added, and the mixture re-evaporated to dryness. The solid residue was dissolved in 4.4M HCl/dioxane (20 ml), the solution evaporated to dryness, and the residue redissolved in dioxane (100 ml) and lyophilized to give N-(N$^\alpha$-benzyloxycarbonyl-$\beta$-benzyl-L-aspartyl)-R-1,1-diaminoethane hydrochloride (10.2 g), which was homogeneous by TLC.

H. The product from Part G (6.6 g, 15 mmole) was dissolved in dry tetrahydrofuran (150 ml) and treated with 2,2,5,5-tetramethylcyclopentanecarboxyl chloride (from Part F; 3.1 g, 15 mmole) followed by triethylamine (4.2 ml, 30 mmole). The reaction mixture was stirred at room temperature for one hour, ethyl acetate added, and the product worked up in the usual manner. Crystallization from ethyl acetate/hexanes gave N-(N$^\alpha$-benzyloxycarbonyl-$\beta$-benzyl-L-aspartyl)-N'-(2,2,5,5-tetramethylcyclopentanecarbonyl)-R-1,1-diaminoethane (6.0 g), which was homogeneous by TLC, m.p. 122°–125° C. The nmr spectrum was consistent with the assigned structure.

I. The product from Part H (5.5 g) was hydrogenated in the usual manner in glacial acetic acid (200 ml) over 10% palladium on carbon. After lyophilization from water several times, the solid residue was crystallized from ethanol/hexanes to give N-(L-aspartyl)-N'-(2,2,5,5-tetramethylcyclopentanecarbonyl)-R-1,1-diaminoethane (2.0 g), m.p. 171°–172° C. The compound was homogeneous by high pressure liquid chromatography (HPLC) (Conditions: Lichrosorb RP-18; linear gradient of 24–33% acetonitrile in 0.01M triethylammonium phosphate, pH 4.5; flow rate=1 ml/min.; retention time=12.31 min.).

Sweetness=800–1000×sucrose.

EXAMPLE 15

N-(L-Aspartyl)-N'-(2,6-Dimethylcyclohexanecarbonyl)-R-1,1-Diaminoethane

[Formula I, R=CH$_3$, R'=H, R''=2,6-dimethylcyclohexyl]

A. Methyltriphenylphosphonium bromide (286 g, 0.80 mole) was suspended in ether (1500 ml) and treated with n-butyllithium (1.6M in ether; 500 ml, 0.80 mole), followed by 2,6-dimethylcyclohexanone (50.4 g, 0.40 mole), following the procedure described in Example 12, Part A. The crude product was distilled to give 1-methylene-2,6-dimethylcyclohexane (24 g), b.p. 146°–154° C./760 mm.

B. The product from Part A (24 g, 0.10 mole) was dissolved in dry tetrahydrofuran (50 ml) and treated under nitrogen with 1M borane-tetrahydrofuran in tetrahydrofuran (250 ml). The reaction mixture was stirred overnight at room temperature and treated with 3N aqueous sodium hydroxide (20 ml) dropwise (foaming occurs), followed, dropwise, by 30% aqueous hydrogen peroxide (20 ml). The mixture was refluxed for 30 minutes, sodium chloride added to saturation and the mixture cooled to room temperature with stirring. The phases were separated and the organic phase dried (Na$_2$SO$_4$) and evaporated under reduced pressure to give a quantitative yield of 2,6-dimethylcyclohexylmethanol. The product was purified by fractionation in vacuo b.p. 187°–210° C./760 mm.

C. The product from Part B (20 g, 0.14 mole) was dissolved in ether (300 ml) and added to a solution of potassium dichromate (90 g, 0.30 mole) in concentrated sulfuric acid (175 ml) and water (900 ml) in an ice bath. The mixture was warmed to room temperature and stirred for 2 days. The phases were separated, the organic phase washed with water, dried (MgSO$_4$) and evaporated under reduced pressure. The residue was fractionated to give 2,6-dimethylcyclohexanecarboxylic acid (16.7 g), which was pure by GC, b.p. 145°–148° C.

D. The product from Part C (16.7 g) was dissolved in tetrahydrofuran (100 ml) and treated with excess thionyl chloride (30 ml) at room temperature. After stirring at room temperature for one hour, the solvent and excess thionyl chloride were evaporated under reduced pressure to provide a quantitative yield of 2,6-dimethylcyclohexanecarboxyl chloride which was used without further purification.

E. N$^\alpha$-Benzyloxycarbonyl-$\beta$-benzyl-L-aspartyl-D-alanyl amide (Example 1, Part B) (10.7 g, 25 mmole) was treated with iodobenzene bis(trifluoroacetate) using the procedure described in Example 5, Part A. The resulting solution was treated with potassium bicarbonate (20 g, 200 mmole), followed by 2,6-dimethylcyclohexanecarboxyl chloride (6.1 g, 35 mmole) added dropwise over 2 minutes. The reaction mixture was stirred for 3 hours at room temperature, and then worked up in the usual manner, except that the product crystallized during drying of the final extracts over Na$_2$SO$_4$. The solution was therefore heated to boiling, filtered hot and the Na$_2$SO$_4$ washed with ethyl acetate. The filtrate was evaporated under reduced pressure and the residue recrystallized from ethyl acetate to give N-(N$^\alpha$-benzyloxycarbonyl-$\beta$-benzyl-L-aspartyl)-N'-(2,6-dimethylcyclohexanecarbonyl)-R-1,1-diaminoethane, (4.5 g) which was homogeneous by TLC, m.p. 146°–150° C. The nmr spectrum of the product was consistent with the assigned structure.

F. The product from Part E (4 g) was hydrogenated in the usual manner in glacial acetic acid (150 ml) over 10% palladium on carbon. After lyophilization from water several times, the solid residue was crystallized from ethanol/water to give N-(L-aspartyl)-N'-(2,6- dimethylcyclohexanecarbonyl)-R-1,1-diaminoethane (0.8 g).

Sweetness = 150–200 × sucrose.

EXAMPLE 16

N-(L-Aspartyl)-N'-(2-t-Butylcyclohexanecarbonyl)-R-1,1-Diaminoethane

[Formula I, R=CH₃, R'=H,
R''=2-t-butylcyclohexyl]

A. Methyltriphenylphosphonium bromide (346 g, 0.97 mole) was suspended in ether (1500 ml) and treated with n-butyllithium (2.5M in ether; 388 ml, 0.97 mole), followed by 2-t-butylcyclohexanone (50 g, 0.324 mole), following the procedure described in Example 12, Part A. The reaction mixture was heated under reflux for 2 days and then worked up in the usual manner. The crude product was fractionated to provide methylene-2-t-butylcyclohexane (22 g), which was pure by GC.

B. The product from Part A (22 g, 0.146 mole) was dissolved in dry tetrahydrofuran (50 ml) and treated under nitrogen with boranetetrahydrofuran in tetrahydrofuran (1M; 160 ml, 0.16 mole). The reaction mixture was stirred at room temperature for 2 days and treated with 4N aqueous sodium hydroxide (40 ml) dropwise (foaming occurs), followed by 30% aqueous hydrogen peroxide (40 ml). The reaction mixture was refluxed overnight and then quenched with ice water, extracted with ether and the combined extracts dried (MgSO₄). The solvent was evaporated under reduced pressure to give 2-t-butylcyclohexylmethanol (17 g) which was used without further purification.

C. The product from Part B (15 g, 0.088 mole) was added to a solution of potassium dichromate (51.8 g, 0.176 mole) in sulfuric acid (102 ml) and water (600 ml). The reaction mixture was stirred at room temperature until all of the starting material had disappeared by GC. The reaction was quenched with water, extracted with ether and the combined extracts dried (MgSO₄). The solvent was evaporated under reduced pressure to give 2-t-butylcyclohexanecarboxylic acid (10 g) which was used without further purification.

D. The product from Part C (10 g, 0.054 mole) was dissolved in pyridine:ether (1:1, 100 ml) and treated with an excess of thionyl chloride (12 ml, 0.162 mole). The reaction mixture was stirred at room temperature for 12 hours and then evaporated under reduced pressure. The residue was fractionated to give 2-t-butylcyclohexanecarboxyl chloride (7 g).

E. N-(N$^\alpha$-Benzyloxycarbonyl-$\beta$-benzyl-L-aspartyl)-R-1,1-diaminoethane hydrochloride (8.52 g, 20 mmole), prepared as described in Example 14, Part G, was dissolved in dry tetrahydrofuran (200 ml) and treated with 2-t-butylcyclohexanecarboxyl chloride (from Part D; 4.05 g, 20 mmole), followed by triethylamine (5.6 ml, 40 mmole). The reaction mixture was stirred at room temperature for 3 hours, ethyl acetate added and the product worked up in the usual manner. Crystallization from ethyl acetate/hexanes gave N-(N$^\alpha$-benzyloxycarbonyl-$\beta$-benzyl-L-aspartyl)-N'-(2-t-butylcyclohexanecarbonyl)-1,1-diaminoethane (4.5 g), which was homogeneous by TLC, m.p. 165°–166° C. The nmr spectrum of the product was consistent with the assigned structure.

F. The product from Part E (4 g) was hydrogenated in the usual manner in glacial acetic acid (150 ml) over 10% palladium on carbon. After lyophilization several times from water, the solid residue was crystallized from isopropanol/water to give N-(L-aspartyl)-N'-(2-t-butylcyclohexanecarbonyl)-R-1,1-diaminoethane (1.5 g), m.p. 195°–198° C.

Sweetness = 150–200 × sucrose.

EXAMPLE 17

N-(L-Aspartyl)-N'-(2,2,5,5-Tetramethylcyclopentanecarbonyl)-R-1,1-Diamino-2-Hydroxyethane

[Formula I, R=CH₂OH, R'=H,
R''=2,2,5,5-tetramethylcyclopentyl]

A. O-Benzyl-D-serine (5.0 g, 25.6 mmole) was dissolved in dimethylformamide (50 ml), treated with chlorotrimethylsilane (3.053 g, 28.1 mmole) and the mixture stirred at room temperature until a homogeneous solution was obtained (approx. 1 hour). Meanwhile, N-benzyloxycarbonyl-$\beta$-benzyl-L-aspartic acid (9.14 g, 25.6 mmole) was dissolved in a 1:1 mixture of dimethylformamide and tetrahydrofuran, cooled to −15° C. and treated with N-methylmorpholine (2.81 ml, 25.6 mmole), followed by isobutyl chloroformate (3.32 ml, 25.6 mmole). After 10 minutes' activation, the precooled solution of O-benzyl-D-serine silyl ester was added, followed by dropwise addition of N-methylmorpholine (2.81 ml, 25.6 mmole), ensuring that the temperature of the reaction mixture was maintained at −15° C. The solution was allowed to warm to room temperature slowly and stirred for 4 hours before acidifying to pH 1–2 (with cooling) using aqueous hydrochloric acid. Chloroform was added, the phases separated and the aqueous layer re-extracted with chloroform. The combined organic extracts were washed with 1N hydrochloric acid (3×) and with saturated sodium chloride and dried (MgSO₄) The solvent was evaporated under reduced pressure and the solid residue crystallized from ethyl acetate/hexanes to give N$^\alpha$-benzyloxycarbonyl-$\beta$-benzyl-L-aspartyl-O-benzyl-D-serine (11.0 g), m.p. 107°–108° C., which was homogeneous by TLC. The nmr spectrum of the product was consistent with the assigned structure.

B. The product from Part A (10.0 g, 18.72 mmole) was dissolved in dimethylformamide (100 ml), cooled to −15° C. and treated with N-methylmorpholine (2.05 ml, 18.72 mmole), followed by isobutyl chloroformate (2.43 ml, 18.72 mmole). After 4 minutes' activation at −15° C., 1-hydroxybenzotriazole ammonium salt (3.13 g, 20.5 mmole) was added as a solid and the mixture stirred at −15° C. for 30 minutes. After warming to room temperature with stirring over 4 hours, chloroform and water were added, the phases separated and the aqueous phase re-extracted with chloroform. The combined organic phases were washed with 1N hydrochloric acid (3×), saturated aqueous sodium bicarbonate (3×), saturated sodium chloride and dried (MgSO₄) The solvent was evaporated under reduced pressure and the solid residue recrystallized from ethyl acetate/hexanes to give N$^\alpha$-benzyloxycarbonyl-$\beta$-benzyl-L-aspartyl-O-benzyl-D-seryl amide (7.4 g), m.p. 150° C. which was homogeneous by TLC. The nmr spectrum of the product was consistent with the assigned structure.

C. The product from Part B (5.33 g, 10 mmole) was dissolved in acetonitrile (50 ml) and the solution diluted with an equal volume of water. Iodobenzene bis(trifluoroacetate) (4.8 g, 11.2 mmole) was then added and the reaction mixture stirred at room temperature for 5 hours. The solution was evaporated under reduced pressure and the residue redissolved in anhydrous HCl/dioxane (4N) and the solution lyophilized to give N-(N$^\alpha$-benzyloxycarbonyl-$\beta$-benzyl-L-aspartyl)-R-1,1-diamino-2-hydroxyethane hydrochloride in quantitative yield which was used without further purification.

D. The product from Part C was dissolved in tetrahydrofuran (50 ml), N-methylmorpholine (3.30 ml, 30 mmole) added, followed by 2,2,5,5-tetramethylcyclopentanecarbonyl chloride (3.1 g, 16 mmole) and the mixture stirred at room temperature for 4 hours. Ethyl acetate and water were added, the phases separated and the aqueous phase re-extracted with ethyl acetate. The combined organic phases were washed with 1M sodium bicarbonate (2×), 2N hydrochloric acid (3×), again with 1M sodium bicarbonate (2×), finally with saturated sodium chloride and dried (MgSO$_4$). The solution was filtered, the filtrate evaporated under reduced pressure and the residue crystallized from ethyl acetate/hexanes to give N-(N$^\alpha$-benzyloxycarbonyl-$\beta$-benzyl-L-aspartyl)-N'-2,2,5,5-tetramethylcyclopentanecarbonyl-1,1-diamino-2-hydroxyethane (4.0 g), m.p. 90°–93° C., which was homogeneous by TLC. The nmr spectrum of the product was consistent with the assigned structure.

E. The product from Part D (3.8 g) was hydrogenated in the usual manner in glacial acetic acid (150 ml) over 10% palladium on carbon. After lyophilization and relyophilization from water several times, N-(L-aspartyl)-N'-(2,2,5,5-tetramethylcyclopentanecarbonyl)-R-1,1-diamino-2-hydroxyethane was obtained in quantitative yield, m.p. 174°–176° C. dec.

Sweetness = 400–500 × sucrose.

EXAMPLE 18

N-(L-Aspartyl)-N'-(2,2,5,5-Tetramethylcyclopentanecarbonyl)-S-1,1-Diaminoethane

[Formula I, R=H, R'=CH$_3$,
R''=2,2,5,5-tetramethylcyclopentyl]

A. N$^\alpha$-benzyloxycarbonyl-$\beta$-benzyl-L-aspartic acid (1.70 g, 5 mmole) was dissolved in tetrahydrofuran (100 ml), the solution cooled to −15° C. and treated with N-methylmorpholine (0.55 ml, 5 mmole). After 10 minutes' activation at −15° C., a precooled solution of L-alanineamide hydrochloride (0.75 g, 6 mmole) in dimethylformamide (50 ml) was added, followed by N-methylmorpholine (0.66 ml, 6 mmole). The solution was allowed to warm to room temperature and stirred overnight. Chloroform and water were then added, the phases separated and the aqueous phase re-extracted with chloroform. The combined organic phases were washed with 1N hydrochloric acid (3×), saturated sodium chloride and dried (MgSO$_4$). The solution was filtered, the filtrate evaporated under reduced pressure and the residue crystallized from ethyl acetate/hexanes to give N$^\alpha$-benzyloxycarbonyl-$\beta$-benzyl-L-aspartyl-L-alanyl amide (2.0 g), m.p. 180°–180.5° C. which was homogeneous by TLC. The nmr spectrum of the product was consistent with the assigned structure.

B. The product from Part A (1.0 g, 4.4 mmole) was dissolved in acetonitrile (25 ml), diluted with an equal volume of water and treated with iodobenzene bis(trifluoroacetate) (2.13 g, 5 mmole). After stirring the solution at room temperature for 5 hours the product was worked up as described in Example 17, Part C, to give N-(N$^\alpha$-benzyloxycarbonyl-$\beta$-benzyl-L-aspartyl)-S-1,1-diaminoethane hydrochloride in quantitative yield, which was used without further purification.

C. The product from Part B was dissolved in tetrahydrofuran (100 ml), N-methylmorpholine (1.1 ml, 10 mmole) added, followed by 2,2,5,5-tetramethylcyclopentanecarbonyl chloride (1.25 g, 6.5 mmole) and the mixture stirred at room temperature for 5 hours. Ethyl acetate and water were then added, the phases separated and the aqueous phase re-extracted with ethyl acetate. The combined organic phases were washed with 1M sodium bicarbonate (2×), 2N hydrochloric acid (3×), again with 1M sodium bicarbonate (2×), finally with saturated sodium chloride and dried (MgSO$_4$). The solution was filtered, the filtrate evaporated under reduced pressure and the residue crystallized from ethyl acetate/hexanes to give N-(N$^\alpha$-benzyloxycarbonyl-$\beta$-benzyl-L-aspartyl)-N'-(2,2,5,5-tetramethylcyclopentanecarbonyl)-S-1,1-diaminoethane (1.3 g), m.p. 129°–131° C. which was homogeneous by TLC. The nmr spectrum of the product was consistent with the assigned structure.

D. The product from Part C was hydrogenated in the usual manner in glacial acetic acid (50 ml) over 10% palladium on carbon. After lyophilization and relyophilization from water several times, N-(L-aspartyl)-N'-(2,2,5,5-tetramethylcyclopentanecarbonyl)-S-1,1-diaminoethane was obtained in quantitative yield, m.p. 174°–176° C. dec. The compound was homogeneous by HPLC (Conditions: see Example 14; retention time = 10.27 min.).

Sweetness = 600–800 × sucrose.

EXAMPLE 19

N-(L-Aspartyl)-N'-(2,2,5,5-Tetramethylthietane-3-carbonyl)-R-1,1-Diaminoethane

[Formula I, R=CH$_3$, R'=H,
R''=2,2,4,4-tetramethylthietane-3-yl]

A. A solution of 1,3-dithiane (25.0 g, 0.208 mole) in tetrahydrofuran (200 ml) was cooled to −30° C. and treated with a solution of n-butyllithium in hexane (2.5M, 83.17 ml, 0.208 mole). The reaction mixture was stirred at this temperature for one hour, the bath lowered to −78° C. and chlorotrimethylsilane (26.4 ml, 0.208 mole) added dropwise. The reaction mixture was stirred at −78° C. for two hours and then quenched at 0° C. with water. The mixture was then extracted twice with ether, the organic extracts combined, dried (MgSO$_4$) and evaporated under reduced pressure to give trimethylsilyldithiane (38.0 g) as a pale yellow oil. The product was >95% pure by GC and was used without further purification.

B. The product from Part A (27.08 g, 0.174 mole) was dissolved in tetrahydrofuran (150 ml), cooled to −78° C. and treated dropwise with a solution of n-butyllithium in hexane (2.5M, 69.44 ml, 0.174 mole). The reaction mixture was stirred at this temperature for one hour and then treated with a solution of 3-oxo-2,2,4,4-tetramethylthietane (25.0 g, 0.174 mole) in tetrahydrofuran (200 ml). The reaction mixture was stirred at −78° C. for two hours, warmed to room temperature and stirred for a further two hours when reaction was 75% complete by GC. A further aliquot of lithio trimethylsilyldithiane (9.61 g, 0.062 mole) was added to complete the reaction. After stirring overnight at room temperature the reaction mixture was quenched with water, extracted with ether (2×), the organic extracts dried (MgSO₄) and evaporated under reduced pressure. The residue was recrystallized from methanol to give 2,2,4,4-tetramethylthietane-3-ketene thioacetal (39.0 g), m.p. 102°–105° C., which was homogeneous by GC. The nmr spectrum of the product was consistent with the assigned structure.

C. The product from Part B (39.0 g, 0.159 mole) was dissolved in aqueous methanol (1:2, v/v, 150 ml), diluted with tetrahydrofuran (50 ml) and treated with p-toluenesulfonic acid (150.7 g, 0.79 mole). The solution was heated under reflux until reaction was complete (disappearance of ketene thioacetal) by GC. The solution was cooled, diluted with water, extracted with ether (2×), the organic extracts dried (MgSO₄) and evaporated under reduced pressure. The solid residue contained 1,3-propanedithio-2,2,4,4-tetramethylthietane-3-carboxylate (29.0 g), m.p. 133°–136° C., which was pure by GC. The nmr spectrum of the product was consistent with the assigned structure.

D. The product from Part C (29.0 g, 0.110 mole) was dissolved in aqueous methanol (1:2, v/v, 150 ml), diluted with tetrahydrofuran (50 ml) and solid potassium hydroxide (61.8 g, 1.10 mole) added. The solution was heated under reflux until reaction was complete (disappearance of the thioester) by GC. The solution was cooled, ether and water added and the phases separated. The ether layer was extracted with water (3×) and the aqueous phases combined, acidified and re-extracted with ether (3×) and hexanes (3×). The combined organic extracts were washed with water, dried (MgSO₄) and evaporated under reduced pressure. The residue was recrystallized from methanol to give 2,2,4,4-tetramethylthietane-3-carboxylic acid (12.1 g), m.p. 149°–151° C. which was pure by GC. The nmr spectrum of the product was consistent with the assigned structure.

E. The product from Part D (10 g, 0.057 mole) was dissolved in tetrahydrofuran (50 ml) and treated with excess thionyl chloride (25 ml). The reaction mixture was stirred at room temperature for 5 hours and then evaporated under reduced pressure to give 2,2,4,4-tetramethylthietane-3-carboxyl chloride in quantitative yield which was used without further purification.

F. D-Alanine (5 g, 0.056 mole) was dissolved in dimethylformamide (100 ml) and treated with chlorotrimethylsilane (6.7 g, 0.063 mole). The reaction mixture was stirred at room temperature until homogeneous (approx. 1 hour). Meanwhile, N$^\alpha$-9-fluorenylmethyloxycarbonyl-β-benzyl-L-aspartic acid (22.3 g, 0.050 mole) was dissolved in dimethylformamide/tetrahydrofuran (1:1, v/v, 200 ml), cooled to −15° C. and treated with N-methylmorpholine (5.5 ml, 0.050 mole) and isobutyl chloroformate (6.5 ml, 0.050 mole). After 10 minutes' activation at −15° C., the precooled solution of D-alanine silyl ester from above was added, followed by a second equivalent of N-methylmorpholine (5.5 ml, 0.050 mole). The reaction mixture was allowed to warm to room temperature, stirred for 3 hours and then acidified (pH 1–2) using aqueous hydrochloric acid. The reaction mixture was stirred for 30 minutes and ethyl acetate added and the phases separated. The aqueous phase was re-extracted with ethyl acetate and the combined organic extracts washed with 1N hydrochloric acid (3×) and dried (MgSO₄). After evaporation of the solvent under reduced pressure the residue was crystallized from ethyl acetate/hexanes to give N$^\alpha$-9-fluorenylmethyloxycarbonyl-β-benzyl-L-aspartyl-D-alanine (22.5 g), m.p. 114°–116° C., which was homogeneous by TLC. The nmr spectrum of the product was consistent with the assigned structure.

G. The product from Part F (20.6 g, 0.040 mole) was dissolved in dimethylformamide (150 ml), cooled to −15° C. and treated with N-methylmorpholine (4.4 ml, 0.040 mole) and isobutyl chloroformate (5.2 ml, 0.040 mole). After 4 minutes' activation at −15° C., 1-hydroxybenzotroazole ammonium salt (9.1 g, 0.060 mole) was added and the mixture stirred at −15° C. for 15 minutes. After warming to room temperature the mixture was stirred for a further 4 hours. Chloroform (large amounts were required because of emulsion formation) and water were added, the phases separated and the organic layer washed with saturated aqueous sodium bicarbonate (3×), 2N hydrochloric acid (3×) and dried (MgSO₄). After evaporation of the solvent under reduced pressure the solid residue was recrystallized from ethyl acetate to give N$^\alpha$-9-fluorenylmethyloxycarbonyl-β-benzyl-L-aspartyl-D-alanyl amide (5.6 g) m.p. 200°–204° C., which was homogeneous by TLC. The nmr spectrum of the product was consistent with the assigned structure.

H. The product from Part G (2 g, 3.0 mmole) was dissolved in acetonitrile/water (1:1, v/v, 500 ml) and treated with iodobenzene bis(trifluoroacetate) (1.9 g, 4.4 mmole). The reaction mixture was stirred overnight at room temperature, evaporated to dryness and the product dissolved in HCl/dioxane (4N) and re-evaporated. The process was repeated and the product finally redissolved in dioxane and lyophilized to give N-(N$^\alpha$-9-fluorenylmethyloxycarbonyl-β-benzyl-L-aspartyl)-R-1,1-diaminoethane hydrochloride in quantitative yield which was used without further purification.

I. The product from Part H was dissolved in tetrahydrofuran (50 ml) and treated with 2,2,4,4-tetramethylthietane-3-carboxyl chloride (from Part E, 1.35 g, 7 mmole) followed by N-methylmorpholine (1.32 ml, 12 mmole). The reaction mixture was stirred for a further 20 minutes. Ethyl acetate was then added, the phases separated and the organic phase washed with 2N HCl (3×), saturated aqueous sodium bicarbonate (3×) and dried (MgSO₄). The solvent was evaporated under reduced pressure and the residue crystallized from ethyl acetate/hexanes to give N-(N$^\alpha$-9-fluorenylmethyloxycarbonyl-β-benzyl-L-aspartyl)-N'-(2,2,4,4-tetramethylthietane-3-carbonyl)-R-1,1-diaminoethane (1.5 g) which was homogeneous by TLC. The nmr spectrum of the product was consistent with the assigned structure.

J. The product from Part I was dissolved in a mixture of methanol (20 ml) and aqueous potassium hydroxide (1N, 20 ml). A precipitate formed immediately which partially dissolved on addition of tetrahydrofuran (10 ml). The mixture was stirred at room temperature for 5 hours and then acidified (pH 5) with acetic acid. After stirring for several hours at room temperature, the mixture was concentrated under reduced pressure and the solution filtered. The filtrate was lyophilized and the residue recrystallized from ethanol/hexanes to give N-(L-aspartyl)-N'-(2,2,4,4-tetramethylthietane-3-carbonyl)-R-1,1-diaminoethane (0.4 g), m.p. 158°–161° C., which was homogeneous by TLC. The nmr spectrum of the product was consistent with the assigned structure.

Sweetness = 150–200 × sucrose.

EXAMPLE 20

N-(L-Aspartyl)-N'-(Cyclopentanecarbonyl)-2,2-Diaminopropane

[Formula I, R=R'=CH₃, R''=cyclopentyl]

A. α-Aminoisobutyric acid (20 g, 0.194 mole) was suspended in tetrahydrofuran (400 ml), treated with a solution of phosgene in toluene (3M, 160 ml) and the mixture heated at 65° C. overnight. The resulting clear solution was evaporated under reduced pressure, redissolved in tetrahydrofuran and re-evaporated to give α-aminoisobutyric acid N-carboxyanhydride as a thick oil which was used without further purification.

B. The product from Part A was dissolved in tetrahydrofuran (200 ml), cooled to −20° C. and treated with excess ammonia gas. The solution was allowed to warm to room temperature slowly and then evaporated to dryness under reduced pressure. The solid residue was extracted with ethyl acetate using a soxhlet extractor over 3 hours, the resultant solution filtered and the product allowed to crystallize. α-Aminoisobutyramide was obtained as a crystalline solid (10 g), m.p. 115°–118° C., which was homogeneous by TLC. The nmr spectrum of the product was consistent with the assigned structure.

C. N$^\alpha$-Benzyloxycarbonyl-β-benzyl-L-aspartic acid (24.2 g, 67 mmole) was dissolved in dry dimethylformamide (300 ml), the solution cooled to −20° C. and treated with dicyclohexylcarbodiimide (14.5 g, 71 mmole). After 30 minutes' activation at this temperature a precooled solution of α-aminoisobutyramide (6.9 g, 67 mmole) in dimethylformamide (125 ml) was added and the mixture allowed to warm to room temperature. After stirring for 2 days, the mixture was evaporated to dryness under reduced pressure and the residue purified by flash chromatography on silica gel, eluting with a stepwise gradient of chloroform/hexanes (3:1, v/v), chloroform and then chloroform/methanol (95:5, v/v). The final product to elute was N$^\alpha$-benzyloxycarbonyl-β-benzyl-L-aspartyl-α-aminoisobutyramide (10.0 g) which was homogeneous by TLC. The nmr spectrum of the product was consistent with the assigned structure.

D. The product from Part C (5.0 g, 11 mmole) was dissolved in acetonitrile (30 ml), the solution diluted with an equal volume of water and treated with iodobenzene bis(trifluoroacetate) (5.16 g, 12 mmole). The reaction mixture was stirred at room temperature for 7 hours when reaction was complete by TLC. The solution was evaporated under reduced pressure, the residue dissolved in dioxane (100 ml) and concentrated hydrochloric acid (3 ml) and lyophilized. The process was repeated to give N-(N$^\alpha$-benzyloxycarbonyl-β-benzyl-L-aspartyl)-2,2-diaminopropane hydrochloride in quantitative yield, which was used without further purification.

E. The product from Part D was dissolved in tetrahydrofuran (100 ml) and treated with triethylamine (2.5 g, 24 mmole), followed by cyclopentanecarbonyl chloride (1.75 g, 13.2 mmole). The reaction mixture was stirred at room temperature for 5 hours, filtered and the filtrate evaporated under reduced pressure. The residue was purified by chromatography on silica gel to give N-(N$^\alpha$-benzyloxycarbonyl-β-benzyl-L-aspartyl)-N'-(cyclopentanecarbonyl)-2,2-diaminopropane, which was homogeneous by TLC. The nmr spectrum of the product was consistent with the assigned structure.

F. The product from Part E was hydrogenated in the usual manner in glacial acetic acid (100 ml) over 10% palladium on carbon. After lyophilization and relyophilization from water several times, N-(L-aspartyl)-N'-(cyclopentanecarbonyl)-2,2-diaminopropane was obtained in quantitative yield.

Sweetness = 50–100 × sucrose

EXAMPLE 21

N-(L-Aspartyl)-N'-(2,2,5,5-Tetramethylcyclopentanecarbonyl)-R-1,1-Diaminopropane

[Compound I, R=CH₂CH₃, R'=H, R''=2,2,5,5-tetramethylcyclopentyl]

A. D-α-Amino-n-butyric acid (5.0 g, 48.5 mmole) was dissolved in dimethylformamide (50 ml), treated with chlorotrimethylsilane (6.15 ml, 48.5 mmole) and the mixture stirred at room temperature for 1 hour. Meanwhile, N$^\alpha$-benzyloxycarbonyl-β-benzyl-L-aspartic acid (15.73 g, 45.1 mmole) was dissolved in dimethylformamide (50 ml), cooled to −15° C. and treated with N-methylmorpholine (4.84 ml, 44.1 mmole), followed by isobutyl chloroformate (5.72 ml, 44.1 mmole). After 10 minutes' activation, the precooled solution of D-α-amino-n-butyric acid silyl ester was added, followed by a second equivalent of N-methylmorpholine (4.84 ml, 44.1 mmole). The solution was allowed to warm to room temperature, stirred for 4 hours and then acidified (pH 1–2) with aqueous hydrochloric acid. Chloroform was added, the phases separated and the aqueous layer re-extracted with chloroform. The combined organic phases were washed with 1N hydrochloric acid (3×), saturated sodium chloride and dried (MgSO₄). The solvent was evaporated under reduced pressure and the residue crystallized from ethyl acetate/hexanes to give N$^\alpha$-benzyloxycarbonyl-β-benzyl-L-aspartyl-D-α-amino-n-butyric acid (13.3 g), m.p. 150°–152° C., which was homogeneous by TLC. The nmr spectrum of the product was consistent with the assigned structure.

B. The product from Part A (10.0 g, 22.6 mmole) was dissolved in dimethylformamide (50 ml), cooled to −15° C. and treated with N-methylmorpholine (2.48 ml, 22.6 mmole), followed by isobutyl chloroformate (2.93 ml, 22.6 mmole). After 4 minutes' activation at −15° C., 1-hydroxybenzotriazole ammonium salt (3.84 g, 24.9 mmole) was added as a solid and the mixture stirred at −15° C. for 45 minutes. The reaction mixture was allowed to warm to room temperature slowly, stirred for 4 hours and then diluted with water and chloroform. The phases were separated and the aqueous phase re-extracted with chloroform. The combined organic extracts were washed with 1N hydrochloric acid (3×), saturated aqueous sodium bicarbonate (3×), saturated sodium chloride and dried (MgSO₄). The solvent was evaporated under reduced pressure and the solid residue recrystallized from ethyl acetate/hexanes to give N$^\alpha$-benzylocarbonyl-β-benzyl-L-aspartyl-D-α-amino-n-butyramide (7.5 g), m.p. 170°–171° C., which was homogeneous by TLC. The nmr spectrum of the product was consistent with the assigned structure.

C. The product from Part B (5.0 g, 11.3 mmole) was dissolved in aqueous acetonitrile (1:1, v/v, 100 ml) and treated with iodobenzene bis(trifluoroacetate) (5.85 g, 13.6 mmole). The reaction mixture was stirred at room temperature for 5 hours and evaporated to dryness under reduced pressure. The residue was redissolved in dioxane (50 ml), excess concentrated aqueous hydrochloric acid added, and the solution re-evaporated several times and finally lyophilized from dioxane to give N-(N$^\alpha$-benzyloxycarbonyl-$\beta$-benzyl-L-aspartyl)-R-1,1-diaminopropane hydrochloride in quantitative yield which was used without further purification.

D. The product from Part C was dissolved in tetrahydrofuran (25 ml) and treated with 2,2,5,5-tetramethylcyclopentanecarbonyl chloride (2.56 g, 13.6 mmole), followed by triethylamine (3.46 ml, 24.9 mmole). The mixture was stirred at room temperature and the reaction monitored by TLC. When reaction was complete (approximately 5 hours), ethyl acetate and water were added, the phases separated and the aqueous phase re-extracted with ethyl acetate. The combined organic phases were washed with 1M aqueous sodium bicarbonate (2×), 2N hydrochloric acid (3×), saturated sodium chloride and dried (MgSO$_4$). The solvent was evaporated under reduced pressure and the residue recrystallized from ethyl acetate/hexanes to give N-(N$^\alpha$-benzyloxycarbonyl-$\alpha$-benzyl-L-aspartyl)-N'-(2,2,5,5-tetramethylcyclopentanecarbonyl)-R-1,1 diaminopropane (4.4 g) which was homogeneous by TLC. The nmr spectrum of the product was consistent with the assigned structure.

E. The product from Part D (4.0 g) was hydrogenated in the usual manner in glacial acetic acid (100 ml) over 10% palladium on carbon. After lyophilization and relyophilization from water several times, N-(L-aspartyl)-N'-(2,2,5,5-tetramethylcyclopentanecarbonyl)-R-1,1-diaminopropane was obtained in quantitative yield, m.p. 164° C. dec.

Sweetness = 200–300 × sucrose.

EXAMPLE 22

Stability of N-(L-Aspartyl)-N'-(2,2,5,5-Tetramethylcyclopentanecarbonyl)-R-1,1-Diaminoethane Sweetener The stability of the title sweetener (Example 14) was studied at 90° C. and pH 7.0 and 3.0 in 0.01M phosphate buffer. The disappearance of the compound under these conditions was monitored by quantitative HPLC measurements, under the following conditions: column: Lichrosorb RP-18; flow rate: 1.5 ml/min.; isocratic acetonitrile (17%) in 0.01M triethylammonium phosphate buffer, pH 4.5. The results of these studies are summarized in Table 2.

From these data the half-life of this compound at both pH 3.0 and pH 7.0 is estimated to be a minimum of 20 years at room temperature (25° C.).

TABLE 2

Stability of N—(L-Aspartyl)-N'—(2,2,5,5-Tetramethylcyclopentanecarbonyl)-R-1,1-Diaminoethane Sweetener at pH 7.0 and 3.0

| Time | Percent Sweetener Remaining | |
|---|---|---|
| | pH 7.0 | pH 3.0 |
| 1 hour | 99.6 | 98.9 |
| 3 hours | 98.7 | 96.5 |
| 8 hours | 97.0 | 92.4 |
| 1 day | 92.4 | 83.0 |
| 4 days | 81.0 | 58.2 |

Sweetness Evaluation

The following is an outline of the "sip and spit" method of blind evaluation used to evaluate the sweetness of the compounds of the invention.

Samples were prepared by dissolving a given amount of the sweetener (e.g. 40 mg in 100 ml) in water or coffee. The sweetener concentration was chosen on the basis of preliminary taste evaluation in which the order of magnitude of sweetness was somewhat established. In addition to the experimental sample, three other samples of sucrose were prepared, their concentrations being chosen to bracket the estimated sweetness of the compound being tested. Samples were presented to an expert taste panel for evaluation. The selected judges were asked to evaluate each sample for sweetness intensity by sipping the solution and spitting and to rank the samples in accordance with descending order of sweetness.

The average rank of the experimental sample was computed and the equivalent concentration of sucrose was estimated. The relative sweetness was calculated from this data. If the experimental product was ranked lowest or highest, the experiment was repeated using different sucrose concentrations.

In addition to being sweeteners, the compounds of the present invention are also useful as flavor potentiators. This is confirmed by the following tests:

Flavor Potentiating—Tomato Sauce

To commercial spaghetti sauce, 3 ppm of the following were added:
1. Compound Example 1
2. Compound Example 14
3. Saccharin The sauces were mixed, heated and evaluated hot by an expert panel for flavor level on a scale of 0=none to 8=very strong. The panel also received a blind control product (with nothing added). The results are summarized below:

| Sample | Flavor Level |
|---|---|
| Control | 6.0 |
| Compound Example 1 | 6.7* |
| Compound Example 14 | 7.0* |
| Saccharin | 5.7 |

*Significant at the 95 percent confidence level.

These data clearly indicate that these compounds act as flavor enhancers and that this property is not related to their sweetness properties.

Flavor Potentiating—Mouthwash

To a commercial mouthwash preparation, the following compounds were added at the 1.5 ppm level:
1. Compound Example 1
2. Compound Example 14 In addition, a control (unaltered product) was included. An expert panel was asked to gargle with the mouthwash for 15 seconds and evaluated the flavor intensity immediately and 3 minutes after gargling on a scale of 0=none to 8=very strong. The results are outlined below:

| | 1 minute | 3 minutes |
|---|---|---|
| Control | 5.7 | 2.2 |
| Example 14 | 6.7* | 3.0* |

-continued

|  | 1 minute | 3 minutes |
|---|---|---|
| Example 1 | 6.0 | 3.0* |

*Significant at the 95 percent confidence level.

These data clearly establish the flavor enhancing properties of the compounds of the invention.

While the invention has been described with respect to particular compounds and methods of producing the compounds, it is apparent that variations and modifications of the invention can be made.

What is claimed is:

1. A compound of the formula:

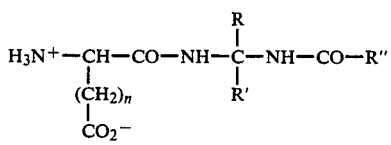

wherein:
n is 0 or 1,
R is lower alkyl, lower hydroxyalkyl or lower thioalkyl,
R' is hydrogen or lower alkyl, and
R" is branched alkyl of 3–10 carbon atoms, cycloalkyl of 3–7 carbon atoms, cycloalkyl substituted by 1–5 lower alkyl groups, lower alkyl-cycloalkyl, dicycloalkyl, heterocycloalkyl wherein the hetero atom is oxygen, nitrogen or sulfur and the cycloalkyl group is of 4–7 carbon atoms, lower alkyl-substituted heterocycloalkyl, fused polycycloalkyl, phenyl or lower alkyl-substituted phenyl.

2. Compound according to claim 1 wherein the fused polycycloalkyl is norbornyl, fenchyl, 1-adamantyl or 2-adamantyl.

3. Compound according to claim 1 wherein the cycloalkyl is of 5–6 carbon atoms.

4. Compound according to claim 1 wherein n=1, R is methyl, R' is hydrogen and R" is cyclopentyl.

5. Compound according to claim 1 wherein n=1, R is methyl, R' is hydrogen and R" is trimethylacetyl.

6. Compound according to claim 1 wherein n=1, R is methyl, R' is hydrogen and R" is norbornyl.

7. Compound according to claim 1 wherein n=1, R is methyl, R' is hydrogen and R" is 2-methylcyclohexyl.

8. Compound according to claim 1 wherein n=1, R is methyl, R' is hydrogen and R" is dicyclopropylmethyl.

9. Compound according to claim 1 wherein n=1, R is methyl, R' is hydrogen and R" is dimethylcyclopentyl.

10. Compound according to claim 1 wherein n=1, R is methyl, R' is hydrogen and R" is tetramethylcyclopentyl.

11. Compound according to claim 1 wherein n=1, R is methyl, R' is hydrogen and R" is dimethlylcyclohexyl.

12. Compound according to claim 1 wherein n=1, R is methyl, R' is hydrogen and R" is t-butylcyclohexyl.

13. Compound according to claim 1 wherein n=1, R is hydroxymethyl, R' is hydrogen and R" is tetramethylcyclopentyl.

14. Compound according to claim 1 wherein n=1, R and R' are methyl and R" is cyclopentyl.

15. Physiologically acceptable cationic and acid addition salts of the compound of claim 1.

16. The compound N-(L-aspartyl)-N'-(2,2,5,5-tetramethylcyclopentanecarbonyl)-1,1-diaminoethane.

17. A composition for sweetening edible materials which comprises a sweetening effective amount of a compound of claim 1 and a nontoxic carrier.

18. A sweetened edible composition, comprising an edible material and a sweetening effective amount of a compound of claim 1.

19. A method of sweetening edible materials, which comprises adding to an edible material a sweetening effective amount of a compound of claim 1.

* * * * *